(12) United States Patent
Chianelli et al.

(10) Patent No.: US 8,563,595 B2
(45) Date of Patent: Oct. 22, 2013

(54) TREATMENT OF CANCER WITH COMPLEX ORGANIC-INORGANIC PIGMENT COMPOSITIONS

(75) Inventors: Russell R. Chianelli, El Paso, TX (US); Siddhartha Das, El Paso, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 326 days.

(21) Appl. No.: 12/618,501

(22) Filed: Nov. 13, 2009

(65) Prior Publication Data

US 2010/0125098 A1 May 20, 2010

Related U.S. Application Data

(60) Provisional application No. 61/114,811, filed on Nov. 14, 2008.

(51) Int. Cl.
*A01N 43/38* (2006.01)
*A61K 31/40* (2006.01)
*C09B 7/02* (2006.01)

(52) U.S. Cl.
USPC .......................................... 514/418; 548/457

(58) Field of Classification Search
None
See application file for complete search history.

(56) References Cited

U.S. PATENT DOCUMENTS

| 6,933,315 B2 * | 8/2005 | Wang et al. .................. 514/414 |
| 2005/0176725 A1 * | 8/2005 | Dent et al. ................ 514/252.18 |
| 2006/0008535 A1 * | 1/2006 | Sabin ........................... 424/630 |

OTHER PUBLICATIONS

Sausville et al. (Cancer Research, 2006, vol. 66, pp. 3351-3354).*
Johnson et al. (British J. of Cancer, 2001, 84(10):1424-1431).*
Aguzzi et al. (Applied Clay Science, 36: 22-36, available online Oct. 9, 2006).*
Gettens, Rutherford J., "Maya Blue: An Unsolved Problem in Ancient Pigments," American Antiquity, (1962), vol. 27, No. 4, pp. 557-564.
Littmann, Edwin R., "Mayya Blue. Further Perspectives and the Possible Use of Indigo as the Colorant," American Antiquity, Apr. 1982, vol. 47, No. 2, pp. 404-408.
Littmann, Edwin R., "Maya Blue. A New Perspective," American Antiquity, Jan. 1980, vol. 45, No. 1, pp. 87-100.
Olphen, H. Van, "Maya Blue: A Clay-Organic Pigment," Science, Nov. 4, 1966, vol. 154, No. 3749, pp. 645-646.
Simon, J.E., et al "Herbs: An Indexed Bibliography," The Scientific Literature on Selected Herbs, and Aromatic and Medicinal Plants of the Temperate Zone, 1984.
Torres, Luis M., "Maya Blue: How the Mayas Could Have Made the Pigment," Mat. Res. Soc. Symp. Proc., (1988), vol. 123, pp. 123-128.

* cited by examiner

*Primary Examiner* — Bong-Sook Baek
(74) *Attorney, Agent, or Firm* — Edwin S. Flores; Chainey P. Singleton; Chalker Flores, LLP

(57) ABSTRACT

The present invention includes compositions and methods for treating disorders of the skin or mucosa resulting from cancer therapies comprising: identifying a patient receiving cancer treatment; and administering to said patient an effective dose of a treated organic/inorganic complex material with an organic dye molecule or derivative thereof, in a pharmaceutically acceptable carrier.

16 Claims, 27 Drawing Sheets

Control

Control

MB 10µL

MB 10µL

Control

Control

Mb 40 µL

Mb 40 µL

Control

Control

MB 50 µL

MB 50 µL

TREATMENT OF CANCER WITH COMPLEX ORGANIC-INORGANIC PIGMENT COMPOSITIONS

CROSS-REFERENCE TO RELATED APPLICATIONS

This application claims priority to U.S. Provisional Application Ser. No. 61/114,811, filed Nov. 14, 2008, the entire contents of which is incorporated herein by reference.

This application is related to U.S. Provisional Application Ser. No. 60/390,049, filed Jun. 19, 2002; U.S. Ser. No. 10/370,288, filed Feb. 18, 2003, now U.S. Pat. No. 7,052,541; U.S. Provisional Application Ser. No. 60/652,105, filed Feb. 11, 2005; U.S. Provisional Application Ser. No. 60/691,683, filed Jun. 17, 2005; U.S. Ser. No. 11/351,577, filed Feb. 10, 2006; and U.S. Ser. No. 11/424,758, filed Jun. 16, 2006, the contents of each herein incorporated by reference in their entirety.

TECHNICAL FIELD OF THE INVENTION

The present invention relates in general to the field of methods for the treatment of cancer, and more particularly, to compositions and methods for the treatment of cancer, e.g., colon and stomach cancers with a complex organic-inorganic pigment.

STATEMENT OF FEDERALLY FUNDED RESEARCH

None.

BACKGROUND OF THE INVENTION

Without limiting the scope of the invention, its background is described in connection with organic/inorganic complexes.

In the scientific literature, the term Maya blue refers to a "turquoise" brilliant shade of blue that is found on murals and archaeological artifacts, for example, throughout Mesoamerica. It is described in the literature as being composed of palygorskite clay and indigo, that when mixed and heated, produce the stable brilliant blue color similar to that found in Mesoamerica. The ancient Mayan Indians would paint unlucky people blue, which was associated with their rain deities, and throw them down a sacred well as human sacrifices. The pigment is known to have the ability to resist age, acid, weathering, and even modern chemical solvents.

Indigo is a dye obtained from many plants, mainly those in the genus *Indigofera*, which are native to the tropics. In ancient times, the dye was obtained by soaking the plant leaves in water and fermenting them in order to convert a "glycoside indican" into the blue dye indigotin. Littman synthesized indigo-attapulgite complexes and verified that his synthetic version was indistinguishable from the original pigments found in the pre-Hispanic murals and artifacts (Littman, 1980; Littman, 1982). The prepared samples had the same physical and chemical characteristics as the authentic Maya blue examined. Littman concluded that the remarkable stability of the attapulgite was due to the heat treatment the attapulgite received during the synthesis. Others have also synthesized compounds similar to that of Maya blue by a number of routes (Torres, 1988). They employed the Gettens test to determine whether the laboratory synthesis of Maya blue was indeed authentic with the same chemical resistant properties (Gettens, 1962). The test was necessary because initial attempts of simply mixing the palygorskite clay produced the color of Maya blue but the mixture did not possess the same chemical properties as the original organic/inorganic complex samples.

Since ancient times, Indigo has been used as an astringent, emetic, stimulant, and antiseptic. In Mexico, the Añil (*Indigofera suffruticosa*) is used for children's headaches by boiling leaves until soft, then apply the leaves like a bandage to the forehead. The Chinese would use *Indigofera tinctoria* L. to clean the liver, detoxify the blood, reduce inflammation, alleviate pain, and reduce fever. In South Africa, the powdered root of *Indigofera* was used to alleviate toothaches.

U.S. Pat. No. 7,052,541 describes color compositions comprising neutral indigo derivative pigments and dyes complexed to the surface of inorganic clays. These materials are useful as paints and coatings for artistic and industrial purposes, including use in cements, plastics, papers and polymers. Upon grinding and heating the organic and inorganic component as solid mixtures or in aqueous solutions, the resulting color compositions have unprecedented stability relative to the original starting materials. Related U.S. Ser. No. 11/351,577, filed Feb. 10, 2006, describes the use of similar starting materials in methods that rely on UV-light for preparing color compositions.

SUMMARY OF THE INVENTION

The present invention includes compositions and methods for treating cancer, e.g., cancers of the stomach and colon. Generally, the present invention includes the use of novel compositions comprising organic/inorganic complexes for the treatment of cancers. The organic dye or pigment can be used alone or complexed with a support during use. As used in this invention, a complex is an organic/inorganic hybrid composition wherein the organic material and the inorganic material interact with each other at the single molecule level or as molecular complexes.

In one embodiment, the present invention includes a method of treating cancer comprising contacting the cancer with a composition comprising a therapeutically effective amount of a treated organic/inorganic complex material with an organic dye molecule derivative thereof, in a pharmaceutically acceptable carrier. In one aspect, the cancer is selected from the group stomach, colon, and breast. In another aspect, the effective amount is 10 to 3,000 mg/kg. In another aspect, the organic dye molecule comprises Maya blue dye is in the form of a prodrug thereof. In another aspect, the composition is micronized and is suitable for administration to the warm blooded animal by injection. In another aspect, the composition is administered in an amount of from 10 mg/kg body weight to 10,000 mg/kg body weight. In another aspect, the composition is administered orally, enterically, intravenously, peritoneally, parenterally or subcutaneously. In another aspect, cancer is a carcinoma, leukemia, melanoma, stomach cancer, colon cancer, breast cancer, lung cancer, brain cancer, pancreatic cancer, ovarian cancer, head and neck cancer, liver cancer or prostate cancer. In another aspect, the cancer involves metastasis and/or a solid tumor. In another aspect, the composition may further comprise a safe and effective amount of a second chemotherapeutic agent.

Another embodiment of the present invention is a method for treating an animal having a tumor of the stomach, color or breast, comprising administering to the animal a therapeutically effective amount of a treated organic/inorganic complex material with an organic dye molecule or derivative thereof, in a pharmaceutically acceptable carrier to induce necrosis in at least a portion of the tumor, induces tumor regression or induces tumor remission. In another aspect, the effective amount is 10 to 3,000 mg/kg. In another aspect, the pigment comprises Maya blue dye is in the form of a prodrug thereof. In another aspect, the composition is micronized and is suitable for administration to the warm blooded animal by injection. In another aspect, the composition is administered in an amount of from 10 mg/kg body weight to 10,000 mg/kg body weight. In another aspect, the composition is administered orally, enterically, intravenously, peritoneally, parenterally or subcutaneously. In another aspect, cancer is a carcinoma, leukemia, melanoma, stomach cancer, colon cancer, breast cancer, lung cancer, brain cancer, pancreatic cancer, ovarian cancer, head and neck cancer, liver cancer or prostate cancer. In another aspect, the cancer involves metastasis and/or a solid tumor. In another aspect, the composition may further comprise a safe and effective amount of a second chemotherapeutic agent.

Another embodiment of the present invention includes a method of treating a cancer comprising administering to a subject in need thereof an effective amount of a composition comprising a therapeutically effective amount of a treated organic/inorganic complex material with an organic dye molecule selected from Maya Blue or indigo dye or a derivative thereof, in a pharmaceutically acceptable carrier, wherein said cancer is selected from the group consisting of a stomach, color or breast cancer. In another aspect, the effective amount is 10 to 3,000 mg/kg. In another aspect, the pigment comprises Maya blue dye is in the form of a prodrug thereof. In another aspect, the composition is micronized and is suitable for administration to the warm blooded animal by injection. In another aspect, the composition is administered in an amount of from 10 mg/kg body weight to 10,000 mg/kg body weight. In another aspect, the composition is administered orally, enterically, intravenously, peritoneally, parenterally or subcutaneously. In another aspect, cancer is a carcinoma, leukemia, melanoma, stomach cancer, colon cancer, breast cancer, lung cancer, brain cancer, pancreatic cancer, ovarian cancer, head and neck cancer, liver cancer or prostate cancer. In another aspect, the cancer involves metastasis and/or a solid tumor. In another aspect, the composition may further comprise a safe and effective amount of a second chemotherapeutic agent.

Yet another embodiment of the present invention is a method for treating disorders of the skin or mucosa resulting from cancer therapies comprising: identifying a patient receiving cancer treatment; and administering to the patient an effective dose of a treated organic/inorganic complex material with an organic dye molecule or derivative thereof, in a pharmaceutically acceptable carrier. In another aspect, the effective amount is 10 to 3,000 mg/kg. In another aspect, the pigment comprises Maya blue dye is in the form of a prodrug thereof.

In another aspect, the composition is micronized and is suitable for administration to the warm blooded animal by injection. In another aspect, the composition is administered in an amount of from 10 mg/kg body weight to 10,000 mg/kg body weight. In another aspect, the composition is administered orally, enterically, intravenously, peritoneally, parenterally or subcutaneously. In another aspect, cancer is a carcinoma, leukemia, melanoma, stomach cancer, colon cancer, breast cancer, lung cancer, brain cancer, pancreatic cancer, ovarian cancer, head and neck cancer, liver cancer or prostate cancer. In another aspect, the cancer involves metastasis and/or a solid tumor. In another aspect, the composition may further comprise a safe and effective amount of a second chemotherapeutic agent.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
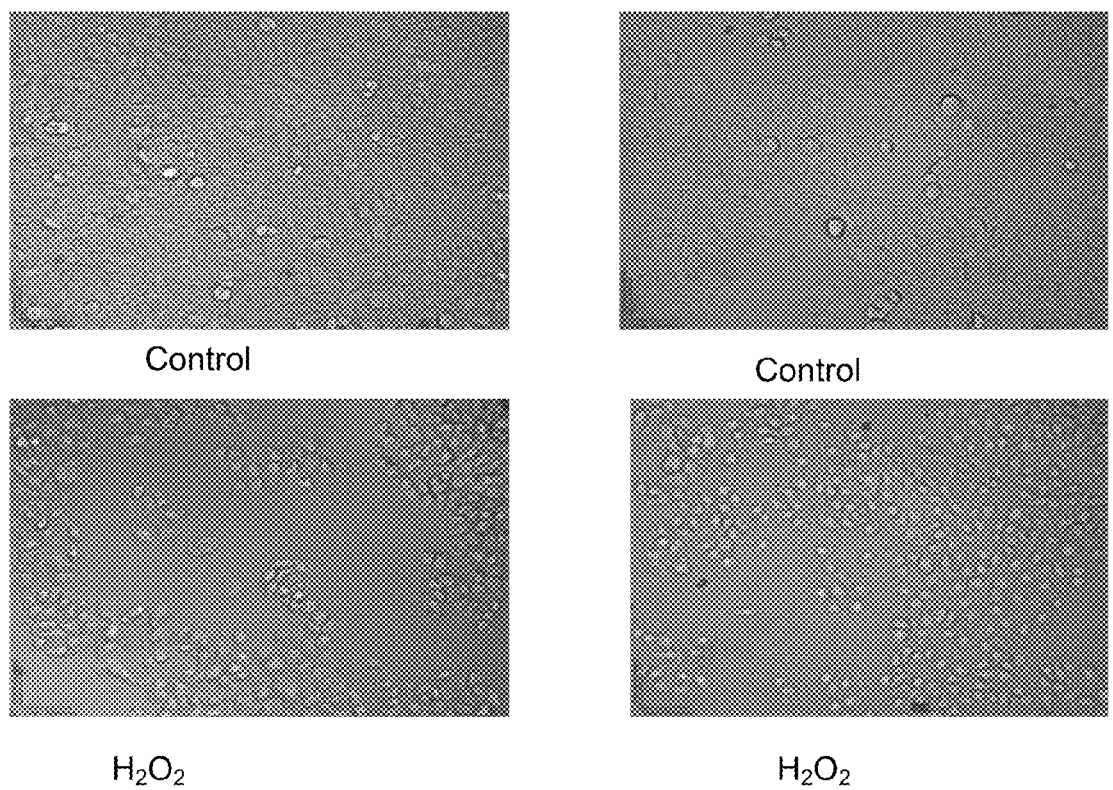
FIG. 1 shows HT-29 cells treated with $H_2O_2$.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention includes a method for treating cancer cells that uses a composition of matter comprising organic pigments and/or dyes complexed with a variety of solid supports based on the Organic/Inorganic Complex Materials with Maya Blue and derivatives thereof. Various Organic/Inorganic Complex Materials with Maya Blue and derivatives thereof may be used with the present invention, including those taught in U.S. Pat. No. 7,052,541, relevant portions incorporated herein by reference. Various methods for making these compositions also are provided and include blending, grinding, heating, and/or treating with light, such as ultraviolet (UV) light or microwave. Alteration of properties during synthesis, such as pH, particle size and support type, will change the color of the final composition. Because of the unique chemical nature of the resulting product, the compositions remain stable over time and under a variety of environmental conditions.

As used herein, the term "therapeutically effective amount" refers to an amount of a Organic/Inorganic Complex Materials with Maya Blue or indigo, or derivatives thereof, effective to yield the desired therapeutic response. For example, an amount effective to delay the growth of or to cause a cancer, either a sarcoma or lymphoma, to shrink or not metastasize. The specific safe and effective amount or therapeutically effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutically acceptable" refers to a component that is suitable for use with humans and/or animals without undue adverse side effects (such as toxicity, irritation, and allergic response) commensurate with a reasonable benefit/risk ratio.

As used herein, the term "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

As used herein, a "pharmaceutical salts" refers to a salt for making an acid or base salt of a compound. Examples of pharmaceutically acceptable salts include, but are not limited to, mineral or organic acid salts of basic residues such as amines; alkali or organic salts of acidic residues such as phenols. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The preferred phenolate salts are the alkaline earth metal salts, sodium, potassium or lithium.

As used herein, a "pharmaceutical carrier" refers to a pharmaceutically acceptable solvent, suspending agent or vehicle, for delivering the Maya Blue dye compound to the animal or human. The carrier may be liquid or solid and is selected with the planned manner of administration in mind. Liposomes are also a pharmaceutical carrier.

As used herein, "cancer" refers to all types of cancer or neoplasm or malignant tumors found in mammals, including carcinomas and sarcomas. Non-limiting examples of cancers are cancer of the brain, breast, cervix, colon, head & neck, kidney, lung, non-small cell lung, melanoma, mesothelioma, ovary, sarcoma, stomach, uterus and medulloblastoma.

As used herein, the phrase "Organic/Inorganic Complex Materials (OICM)" refers to a combination of organic dye molecules (e.g., indigo and its derivatives) and an inorganic material such as palygorskite clay. When the OICM are stabilized using, e.g., heat or exposure to UV light, the organic and inorganic bond is stabilized and both the dye and the clay become more stable. The treatment changes the molecular configuration of the inorganic molecule as seen by a color change upon forming the OICM, thereby changing the properties of the OICM from the two original organic and inorganic molecules. The treatment also results in properties that are superior or different from the original organic molecule, e.g., cancer suppression with indigo based OICM that is larger than with the original indigo molecule alone. Also, the inorganic part may be different from palygorskite that is a fibrous clay. For example, Sepiolite may be used as a fibrous clay, as are layered (Montmorilanite, etc.), Zeolites and other silica alumina materials.

Dosages. A dosage unit for use of the Organic/Inorganic Complex Materials of the present invention, may be a single compound or mixtures thereof with other compounds, e.g., a potentiator. The compounds may be mixed together, form ionic or even covalent bonds. The Maya Blue dye of the present invention may be administered in oral, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., tablets, capsules, pills, powders, granules, elixirs, tinctures, suspensions, syrups, and emulsions may be used to provide the Maya Blue dye of the present invention to a patient in need of therapy that has or is suspected of having a cancer. The Maya Blue dye may also be administered as any one of known salt forms.

The Organic/Inorganic Complex Materials of the present invention may be administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the Organic/Inorganic Complex Materials may be formulated to provide, e.g., maximum and/or consistent dosing for the particular form for oral, rectal, topical, intravenous injection or parenteral administration. While the Organic/Inorganic Complex Materials may be administered alone, it will generally be provided in a stable salt form mixed with a pharmaceutically acceptable carrier. The carrier may be solid or liquid, depending on the type and/or location of administration selected.

Techniques and compositions for making useful dosage forms using the present invention are described in one or more of the following references: Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.), and the like, relevant portions incorporated herein by reference.

For example, the Organic/Inorganic Complex Materials may be included in a tablet. Tablets may contain, e.g., suitable binders, lubricants, disintegrating agents, coloring agents, flavoring agents, flow-inducing agents and/or melting agents. For example, oral administration may be in a dosage unit form of a tablet, gelcap, caplet or capsule, the active drug component being combined with an non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol, mixtures thereof, and the like. Suitable binders for use with the present invention include: starch, gelatin, natural sugars (e.g., glucose or beta-lactose), corn sweeteners, natural and synthetic gums (e.g., acacia, tragacanth or sodium alginate), carboxymethylcellulose, polyethylene glycol, waxes, and the like. Lubricants for use with the invention may include: sodium oleate, sodium stearate, magnesium stearate, sodium benzoate, sodium acetate, sodium chloride, mixtures thereof, and the like. Disintegrators may include: starch, methyl cellulose, agar, bentonite, xanthan gum, mixtures thereof, and the like.

Organic/Inorganic Complex Materials may be administered in the form of liposome delivery systems, e.g., small unilamellar vesicles, large unilamallar vesicles, and multilamellar vesicles, whether charged or uncharged. Liposomes may include one or more: phospholipids (e.g., cholesterol), stearylamine and/or phosphatidylcholines, mixtures thereof, and the like.

Organic/Inorganic Complex Materials may also be coupled to one or more soluble, biodegradable, bioacceptable polymers as drug carriers or as a prodrug. Such polymers may include: polyvinylpyrrolidone, pyran copolymer, polyhydroxylpropylmethacrylamide-phenol, polyhydroxyethylasparta-midephenol, or polyethyleneoxide-polylysine substituted with palmitoyl residues, mixtures thereof, and the like. Furthermore, the Organic/Inorganic Complex Materials may be coupled one or more biodegradable polymers to achieve controlled release of the Organic/Inorganic Complex Materials, biodegradable polymers for use with the present invention include: polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

In one embodiment, gelatin capsules (gelcaps) may include the Organic/Inorganic Complex Materials and powdered carriers, such as lactose, starch, cellulose derivatives, magnesium stearate, stearic acid, and the like. Like diluents may be used to make compressed tablets. Both tablets and capsules may be manufactured as immediate-release, mixed-release or sustained-release formulations to provide for a range of release of medication over a period of minutes to hours. Compressed tablets may be sugar coated or film coated to mask any unpleasant taste and protect the tablet from the atmosphere. An enteric coating may be used to provide selective disintegration in, e.g., the gastrointestinal tract.

For oral administration in a liquid dosage form, the oral drug components may be combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents, mixtures thereof, and the like.

Liquid dosage forms for oral administration may also include coloring and flavoring agents that increase patient acceptance and therefore compliance with a dosing regimen. In general, water, a suitable oil, saline, aqueous dextrose (e.g., glucose, lactose and related sugar solutions) and glycols (e.g., propylene glycol or polyethylene glycols) may be used as suitable carriers for parenteral solutions. Solutions for parenteral administration include generally, a water soluble salt of the active ingredient, suitable stabilizing agents, and if necessary, buffering salts. Antioxidizing agents such as sodium bisulfite, sodium sulfite and/or ascorbic acid, either alone or in combination, are suitable stabilizing agents. Citric acid and its salts and sodium EDTA may also be included to increase stability. In addition, parenteral solutions may include pharmaceutically acceptable preservatives, e.g., benzalkonium chloride, methyl- or propyl-paraben, and/or chlorobutanol. Suitable pharmaceutical carriers are described in Remington's Pharmaceutical Sciences, Mack Publishing Company, a standard reference text in this field, relevant portions incorporated herein by reference.

For direct delivery to the nasal passages, sinuses, mouth, throat, esophagous, tachea, lungs and alveoli, the Organic/Inorganic Complex Materials may also be delivered as an intranasal form via use of a suitable intranasal vehicle. For dermal and transdermal delivery, the Organic/Inorganic Complex Materials may be delivered using lotions, creams, oils, elixirs, serums, transdermal skin patches and the like, as are well known to those of ordinary skill in that art. Parenteral and intravenous forms may also include pharmaceutically acceptable salts and/or minerals and other materials to make them compatible with the type of injection or delivery system chosen, e.g., a buffered, isotonic solution. Examples of useful pharmaceutical dosage forms for administration of Organic/Inorganic Complex Materials may include the following forms.

Capsules. Capsules may be prepared by filling standard two-piece hard gelatin capsules each with 10 to 500 milligrams of powdered active ingredient, 5 to 150 milligrams of lactose, 5 to 50 milligrams of cellulose and 6 milligrams magnesium stearate and the Organic/Inorganic Complex Materials.

Soft Gelatin Capsules. A mixture of Organic/Inorganic Complex Materials is dissolved in a digestible oil such as soybean oil, cottonseed oil or olive oil. The active ingredient is prepared and injected by using a positive displacement pump into gelatin to form soft gelatin capsules containing, e.g., 100-500 milligrams of the active ingredient. The capsules are washed and dried.

Tablets. A large number of tablets are prepared by conventional procedures so that the dosage unit was 100-500 milligrams of Organic/Inorganic Complex Materials, 0.2 milligrams of colloidal silicon dioxide, 5 milligrams of magnesium stearate, 50-275 milligrams of microcrystalline cellulose, 11 milligrams of starch and 98.8 milligrams of lactose. Appropriate coatings may be applied to increase palatability or delay absorption.

To provide an effervescent tablet appropriate amounts of, e.g., monosodium citrate and sodium bicarbonate, are blended together and then roller compacted, in the absence of water, to form flakes that are then crushed to give granulates. The granulates are then combined with the Organic/Inorganic Complex Materials and/or salt thereof, conventional beading or filling agents and, optionally, sweeteners, flavors and lubricants.

Injectable solution. A parenteral composition suitable for administration by injection is prepared by stirring 1% to 10% by weight of Organic/Inorganic Complex Materials in deionized water and mixed with, e.g., up to 10% by volume propylene glycol and water. The solution is made isotonic with sodium chloride and sterilized using, e.g., ultrafiltration.

Suspension. An aqueous suspension of Organic/Inorganic Complex Materials is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

For mini-tablets, the Organic/Inorganic Complex Materials is compressed into a hardness in the range 6 to 12 Kp. The hardness of the final tablets is influenced by the linear roller compaction strength used in preparing the granulates, which are influenced by the particle size of, e.g., the monosodium hydrogen carbonate and sodium hydrogen carbonate. For smaller particle sizes, a linear roller compaction strength of about 15 to 20 KN/cm may be used.

Kits. The present invention also includes pharmaceutical kits useful, for example, for the treatment of cancer, which comprise one or more containers containing a pharmaceutical composition comprising a therapeutically effective amount of Organic/Inorganic Complex Materials. Such kits may further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, may also be included in the kit. It should be understood that although the specified materials and conditions are important in practicing the invention, unspecified materials and conditions are not excluded so long as they do not prevent the benefits of the invention from being realized.

The Organic/Inorganic Complex Materials and other chemotherapeutic agents, e.g., cancer treatment potentiators, are typically mixed with a pharmaceutically acceptable carrier. This carrier can be a solid or liquid and the type is generally chosen based on the type of administration being used. The active agent can be coadministered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

As used herein, the term "potentiator" refers to a compound that accentuates or potentiates a cytotoxic activity upon a cell, e.g., a cell that is targeted using the Organic/Inorganic Complex Materials. The potentiator many be a procodazole, triprolidine, propionic acid, monensin, an antisense inhibitor of the RAD51 gene, bromodeoxyuridine, dipyridamole, indomethacin, a monoclonal antibody, an anti-transferrin receptor immunotoxin, metoclopramide, 7-thia-8-oxoguanosine, N-solanesyl-N,N'-bis(3,4-dimethoxybenzyl)ethylenediamine, N-[4[(4-fluorphenyl)sulfonyl]phenyl]acetamide, leucovorin, heparin, heparin sulfate, cimetidine, a radiosensitizer, a chemosensitizer, a hypoxic cell cytotoxic agent, muramyl dipeptide, vitamin A, 2'-deoxycoformycin, a bis-diketopiperazine derivative having potentiator activity, dimethyl sulfoxide or mixtures thereof. The potentiator may be added in conjunction with the Organic/Inorganic Complex Materials. The potentiator may be added before, during or after a dose of Organic/Inorganic Complex Materials and may even be conjugated directly with the Organic/Inorganic Complex Materials, either covalently or ionically. In one example, the Organic/Inorganic Complex Materials and the potentiator are mixed with a biodegradable resin or matrix that releases the Organic/Inorganic Complex Materials and the potentiator at the same or different rates, at the same or disparate times and combinations thereof.

Dyes. As discussed above, the selection of Organic/Inorganic Complex Materials is based on its ability to kill cancer cells. Thus, in one embodiment, the dye/pigment may be represented by Formula I:

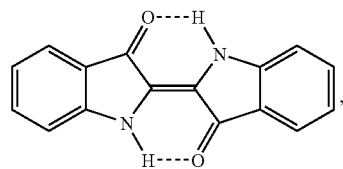

Supports. Compositions of the present invention may also include a support. Though the supports may take a variety of different forms, one feature of the present invention is that the dyes and pigments undergo a chemical or atomic interaction with the support to form a complex. The complex formed is an organic/inorganic hybrid composition. The interactions include coordinate covalent bonding, covalent bonding and/or hydrogen bonding.

Clays. As used herein, the term "clay" refers to fibrous clays. The fibrous clay is preferentially a palygorskite clay, a sepiolite clay, or a mixture of palygorskite and sepiolite clays. The mixture may be in any ratio. For example, it may be 50% palygorskite and 50% sepiolite or it may be 10%/90%, 20%/80%, 30%/70%, 40%/60%, 60%/40%, 70%/30%, 80%/20%, or 90%/10% (palygorskite/sepiolite). As used herein the term palygorskite and attapulgite are used interchangeably to refer to the same type of clay.

Previous work has shown that synthesis of comparable organic/inorganic complex paints using clays with plate-like structures, including kaolinite, bentonite, nontronite, and mordenite all produce a blue colored pigment, but without the stability of the indigo derivative/palygorskite complex (Olphen, 1966a; Olphen, 1966b). This indicates that the possible stability of the Maya blue pigment is due to the fiber-like structure of the clays used since the use of plate-like clays had not been shown to yield a stable pigment (Olphen, 1966a; Olphen, 1966b; Littman, 1980; Littman, 1982).

The particle size of the clay may be varied. It is preferentially between about 0.01 µm and about 40 µm, about 0.05 µm and about 10 µm, or more preferably between about 0.1 µm and about 4 µm. As the color changes with the size of the particles, varying the particle size allows for greater control of color.

Polymers, Binding Agents and Modifiers. In addition to the supports described above, one or more binding agents or modifiers may be added to the compositions to increase stability, uniformity, spreadability, adhesion, coating thickness, etc. Binding agents and modifiers are well known in the art of paint formulation and may be included in the composition. Binding agents such as solvent-containing binding agents (acryl, cyclized rubber, butyl rubber, hydrocarbon resin, α-methylstyrene-acrylonitrile copolymers, polyester imide, acryl acid butyl esters, polyacrylic acid esters, polyurethanes, aliphatic polyurethanes and chloro sulphonated polyethylene), may be added to the composition.

General Methods for Producing Compositions. The general method for producing compositions according to certain embodiments of the present invention comprises providing a dye or pigment as described herein. The amount of dye or pigment used can be in the range of about, at least about, or at most about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, 20.0%, 21%, 22%, 23%, 24% or 25% by weight based on the total weight of the composition or more preferably about 0.1% to about 25% by weight based on the total weight of the composition. The amount of dye or pigment used can be in the range of about 0.01% to about 25% by weight or more preferably about 0.1% to about 25% by weight based on the total weight of the composition. In certain embodiments of the invention the amount of dye or pigment is at least 8% or more by weight based on the total weight of the composition.

The next step comprises combining the dye/pigment with a support, such as a clay, as described herein. When combining with a support, this next step optionally comprises the grinding or mixing of the dye or pigment with the support, for example, in a blender, industrial blender, industrial mixer, shear blender, or a precise solid state blender. The support and the dye/pigment may be ground separately and then ground together or they may be combined and ground to both mix the two components in order to obtain the preferred ratio. Techniques for grinding and blending the dye/pigment and support compositions are found in *Mixing of Solids* (Weinekotter and Gericke, 2000), *Powder and Bulk Solids Handling Processes* (Iinoya et al., 1988), or *Bulk Solids Mixing* (Gyenis and Gyenis, 1999).

The support-containing mixture should be ground to obtain particles of between about 0.005 µm and about 50 µm. In certain embodiments the range of particle sizes is between about 0.01 µm and about 20 µm. In certain embodiments the range of particle sizes is between about 0.05 µm and about 10 µm. In certain embodiments the range of particle sizes is between about 0.1 µm and about 8 µm. A range of particles sizes is expected, but in certain embodiments over 60% of the particles are within the desired range of particle sizes. In certain embodiments over 80% of the particles are within the desired range of particle sizes. In certain embodiments over 90% of the particles are within the desired range of particle sizes. In certain embodiments over 95% of the particles are within the desired range of particle sizes. In certain embodiments over 99% of the particles of the particles are within the desired range of particle sizes.

The next step may comprise heating the composition of ingredients. The heating may comprise heating at a temperature of about 170° C. to about 300° C. The heating may comprise heating at a temperature of about 100° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., 200° C., 205° C., 210° C., 215° C., 220° C., 225° C., 230° C., 235° C., 240° C., 245° C., 250° C., 255° C., 260° C., 265° C., 270° C., 275° C., 280° C., 285° C., 290° C., 295° C. or 300° C., or more. In certain embodiments, the composition is heated to a temperature between about 115° C. and about 200° C. The heating may be for several hours, or may last up to one day. The heating can be carried out in, but not limited to, a batch oven, a drying oven, an infrared oven, or a powder coating oven.

An alternative to heating comprises treating the composition with radiation, including ultraviolet. Light radiation in the range from about 10 nm to about 500 nm can be used in certain embodiments of the present invention, particularly about 200-400 nm (i.e., near UV). Treatment times will vary from very brief—as short as one minute—to several hours (e.g., about 1-48 hours, such as about, at least about, or at most about 1, 2, 3, 4, 5, 7, 8, 9, 10, 11, 12, 18, 24, 36, 48 or more hours). In certain embodiments the radiation treatment can range from about 1 to about 48 hours. Suitable devices for providing UV exposure exist including chambers and reactor vessels.

Next, the pH of the composition may be adjusted to an acidic or neutral pH, depending on the final color desired. Exemplary acids that may be used to adjust the pH comprise: any protonic acid, $H_2SO_4$, $HClO_4$, $HClO_3$, $H_3PO_4$, $HNO_3$, HCN, HF, HBr, HI, $H_3O^+$, or $CH_3COOH$, or more preferably HCl. Exemplary bases that may be used to adjust the pH comprise: LiOH, NaOH, KOH, RbOH, CsOH, $Ca(OH)_2$, $Sr(OH)_2$, $Ba(OH)_2$ or more preferably NaOH. The pH of the composition can range from about 1-12, including about 1, 2, 3, 4, 5, 6, 7, 8, 9, 10, 11, or 12. The pH of the system can be monitored with a pH meter that is calibrated with buffers that range from a pH of about 1-12, including about 1, 2, 3, 4, 5, 6, 7, 8, 9, 10, 11, or 12.

Additional steps in making a final composition may comprise: treating the composition with acid such as but not limited to any protonic acid, $H_2SO_4$, $HClO_4$, $HClO_3$, $H_3PO_4$, $HNO_3$, HCN, HF, HBr, HI, $H_3O^+$, or $CH_3COOH$, or more preferably HCl, to remove impurities from the support; applying the composition to a surface; blending the composition with a polymer, plastic or organic binder as discussed in Encyclopedia of Polymer Science and Engineering, $2^{nd}$ ed. (Herman, 1990) and Paint and Surface Coatings: Theory and Practice, $2^{nd}$ ed. (Lambourne and Strivens, 1999).

Certain embodiments of the present invention may comprise hydrogen and/or coordinate covalent bonding prior to any mixing, blending, heating, irradiation, and/or pH alteration. Compositions may form hydrogen and/or coordinate covalent bonds at any point during combining, mixing, blending, heating, irradiation and/or pH alteration.

The following examples are included to demonstrate certain embodiments of the invention. It should be appreciated by those of skill in the art that the techniques disclosed in the examples which follow represent techniques discovered by the inventor to function well. However, those of skill in the art should, in light of the present disclosure, appreciate that many changes can be made in the specific embodiments which are disclosed and still obtain a like or similar result without departing from the spirit and scope of the invention.

EXAMPLE 1

Killing of Cancer Cells with Maya Blue

An Organic/Inorganic Complex Pigment was used to test the effect of the Organic/Inorganic Complex Materials with Maya Blue dye or Ingido dye was used to test for killing of various cancer cell types. Three different cancer cells were targeted for killing, a human colon cancer cell line, a breast cancer cell line and a lung cancer cell line.

Briefly, an Organic/Inorganic Complex Materials with Maya Blue was used against the following cancer cell lines: HT-29: Human colon adenocarcinoma; MCF-7: Breast Cancer; and CRL: Lung Cancer. A positive control for killing of the cancer cells was $H_2O_2$. The vehicle control used was $H_2O$ and tests were performed in a 96-well plate. For the determination of cell viability, MTS dye (Promega, Wis.) was used and tested using a spectrophotometer.

The Organic/Inorganic Complex Materials with Maya Blue was made into a slurry at 10 mg/mL of water. The cells, 10,000 cells/well, were plated in the 96 well plate and grow overnight in 200 μL of media; keep one lane without cells, only media and that is control for the spectrophotometer. The following day, various concentrations of Organic/Inorganic Complex Materials with Maya Blue were added (at 5 μL, 10 μL, 30 μL, 40 μL, 50 μL along) with the vehicle and positive controls, followed by the MTS assay. Briefly, 12 μL of MTS solution were added to each well and incubated for 40-45 minutes (at 37° C.), or until the color changes to brown in the control. The 96-well plate was reader at 495 nm.

Figure 2:
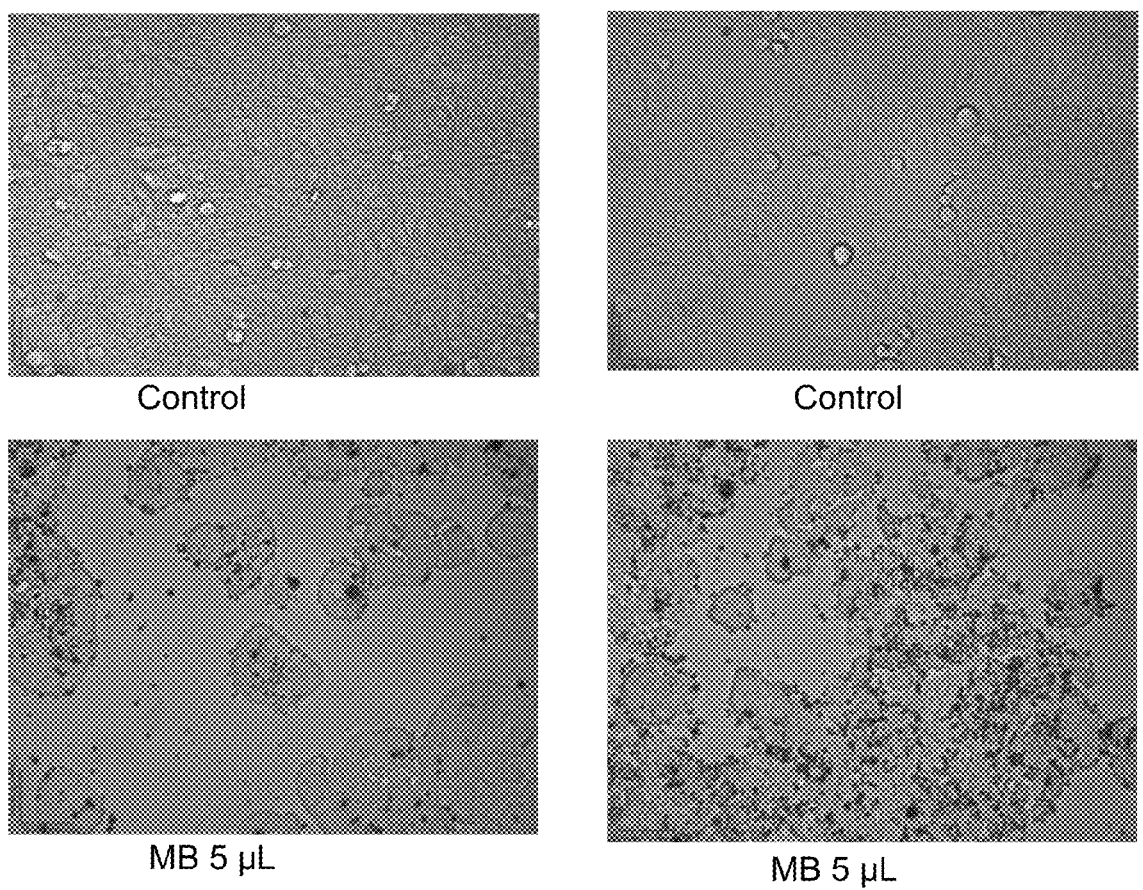
FIG. 2 shows HT-29 cells treated with 5 uL of an Organic/Inorganic Complex Materials with Maya Blue (suspended in water).
Figure 3:
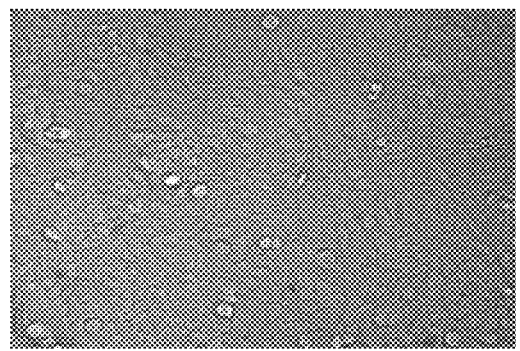
FIG. 3 shows HT-29 cells treated with 10 uL of an Organic/Inorganic Complex Materials with Maya Blue (suspended in water).
Figure 3:
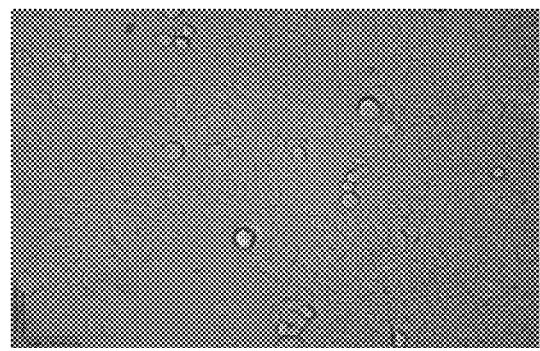
Figure 3:
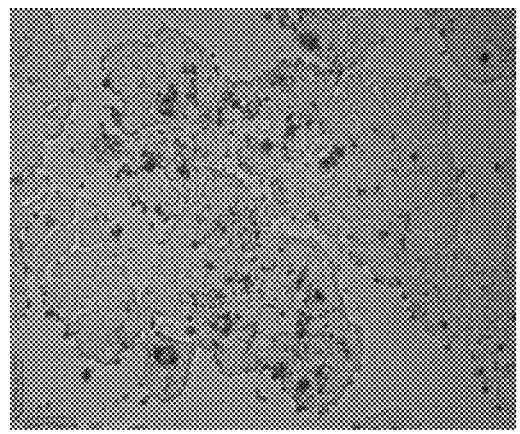
Figure 3:
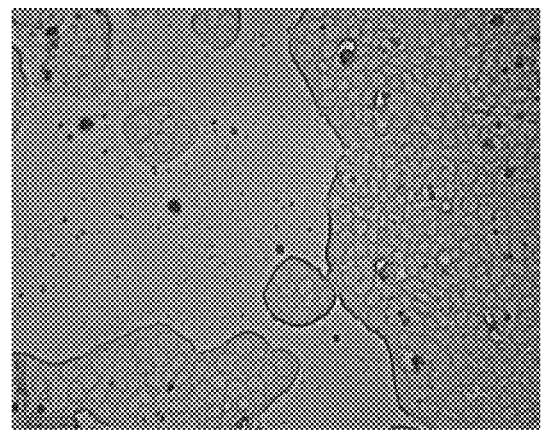
Figure 4:
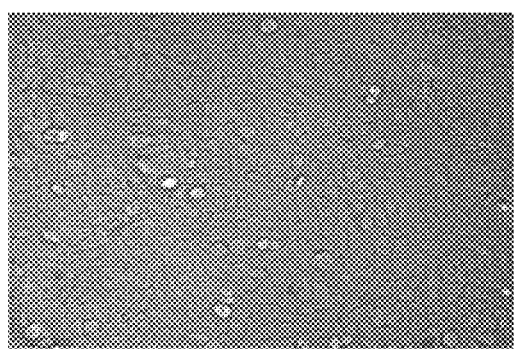
FIG. 4 shows HT-29 cells treated with 30 uL of an Organic/Inorganic Complex Materials with Maya Blue (suspended in water).
Figure 4:
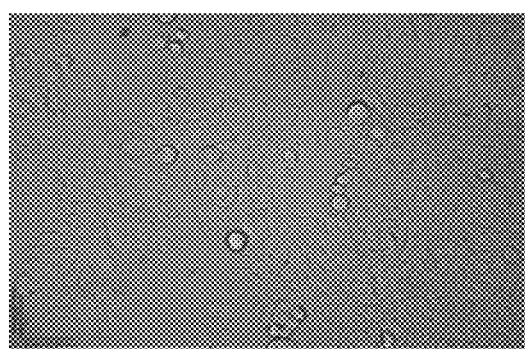
Figure 4:
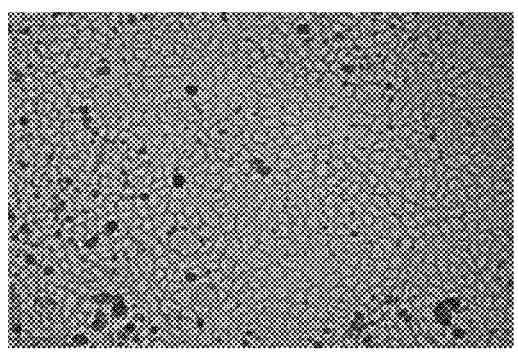
Figure 4:
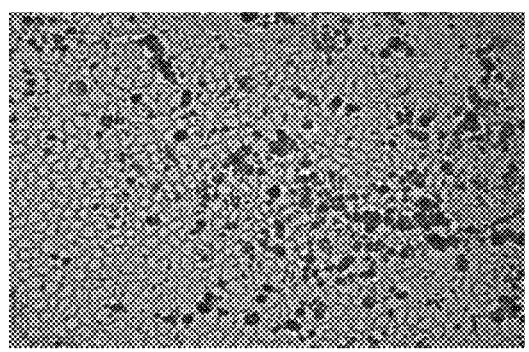
Figure 5:
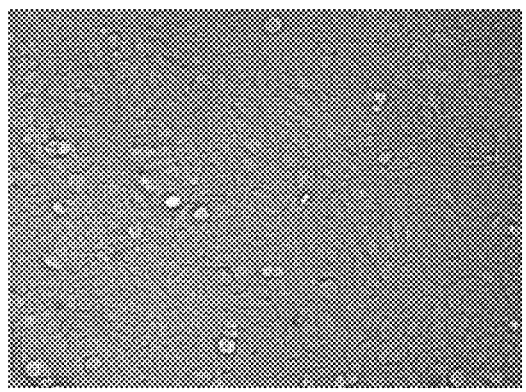
FIG. 5 shows HT-29 cells treated with 40 uL of an Organic/Inorganic Complex Materials with Maya Blue (suspended in water)
Figure 5:
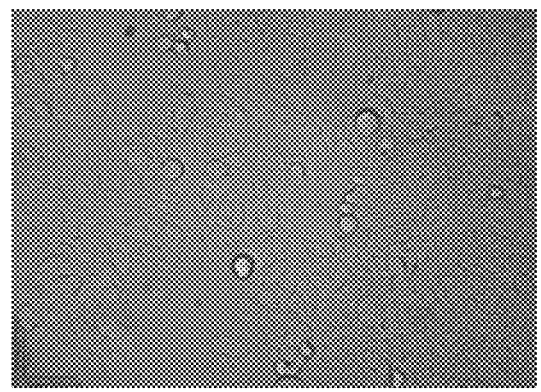
Figure 5:
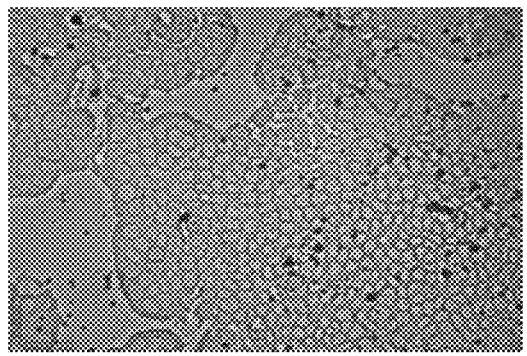
Figure 5:
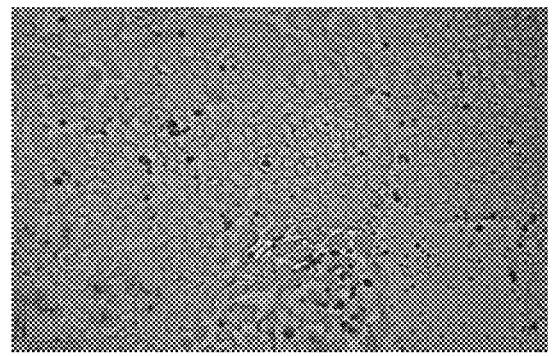
Figure 6:
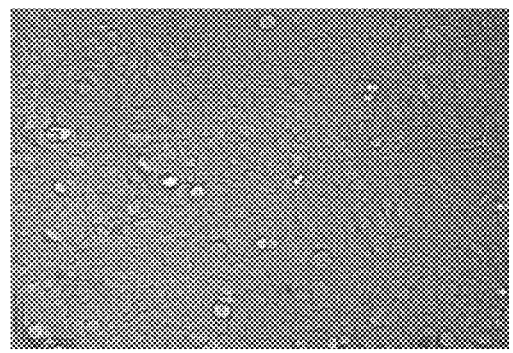
FIG. 6 shows HT-29 cells treated with 50 uL of an Organic/Inorganic Complex Materials with Maya Blue (suspended in water).
Figure 6:
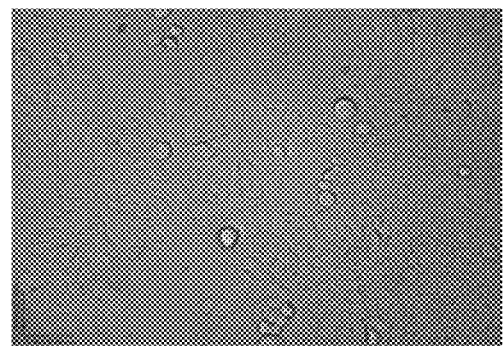
Figure 6:
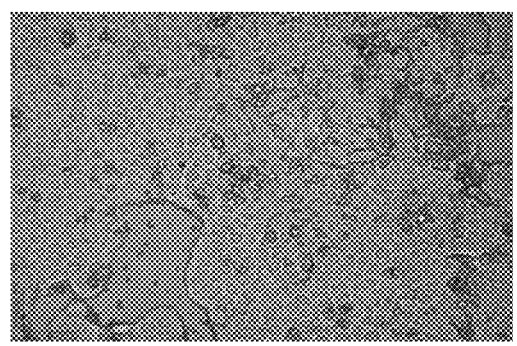
Figure 6:
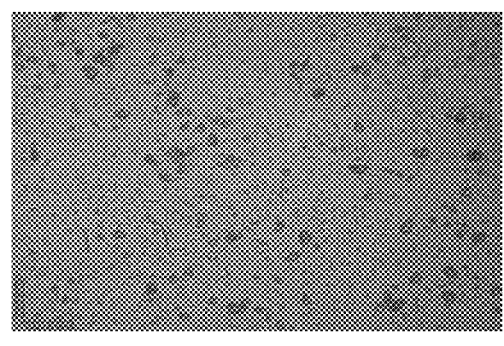
Figure 7:
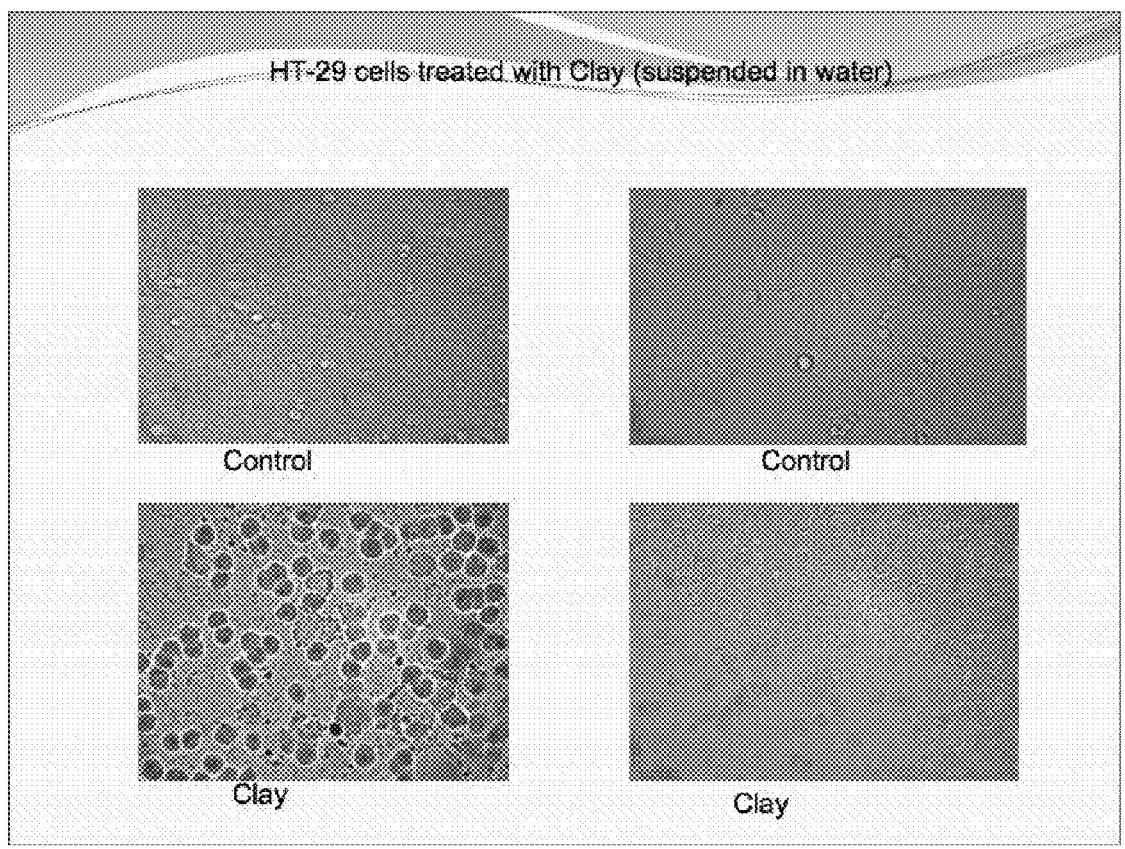
FIG. 7 shows HT-29 cells treated with Indigo (suspended in water).
Figure 8:
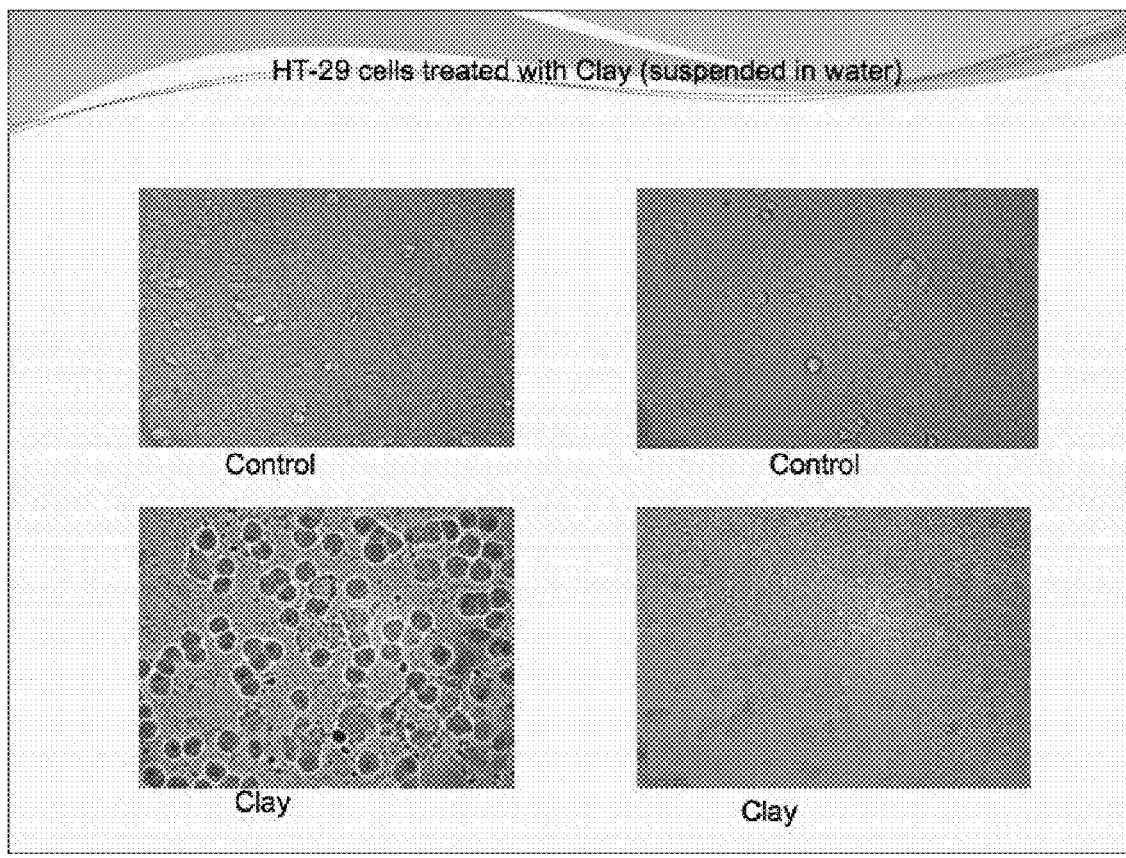
FIG. 8 shows HT-29 cells treated with clay.

FIG. 1 shows HT-29 cells treated with the positive control for cell killing: $H_2O_2$. FIG. 2 shows HT-29 cells treated with different concentrations of Mayan Blue (suspended in water). FIG. 3 shows HT-29 cells treated with different concentrations of Mayan Blue (suspended in water). FIG. 4 shows HT-29 cells treated with different concentrations of Mayan Blue (suspended in water). FIG. 5 shows HT-29 cells treated with different concentrations of Mayan Blue (suspended in water). FIG. 6 shows HT-29 cells treated with different concentrations of Mayan Blue (suspended in water). FIG. 7 shows HT-29 cells treated with Indigo (suspended in water). FIG. 8 shows HT-29 cells treated with clay.

Figure 9:
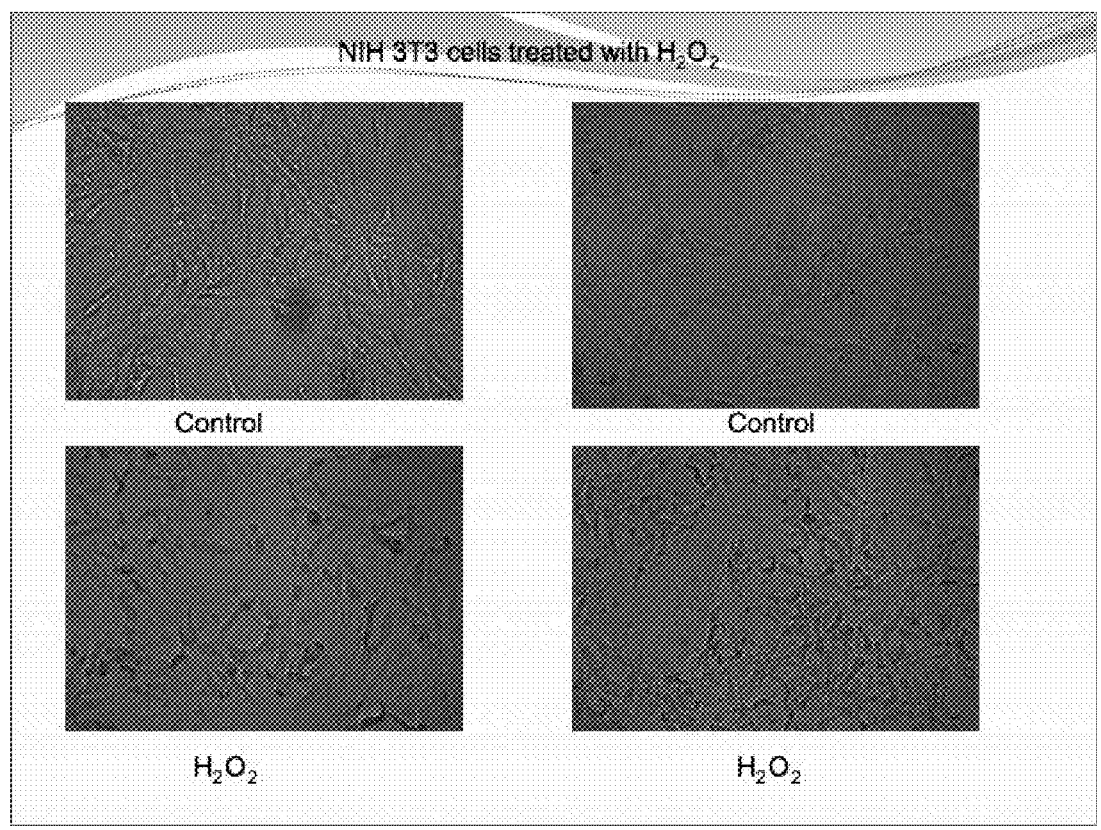
FIG. 9 shows NIH-3T3 cells treated with $H_2O_2$.
Figure 10:
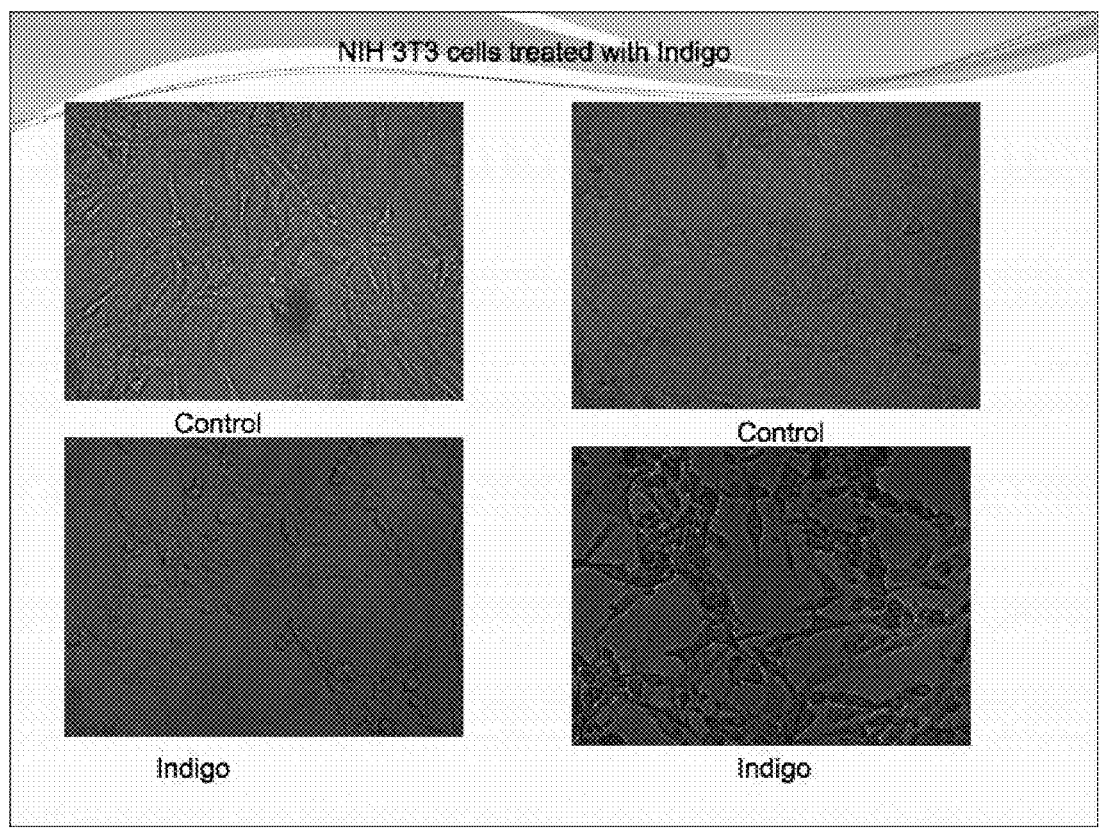
FIG. 10 shows NIH-3T3 cells treated with Indigo (suspended in water).
Figure 11:
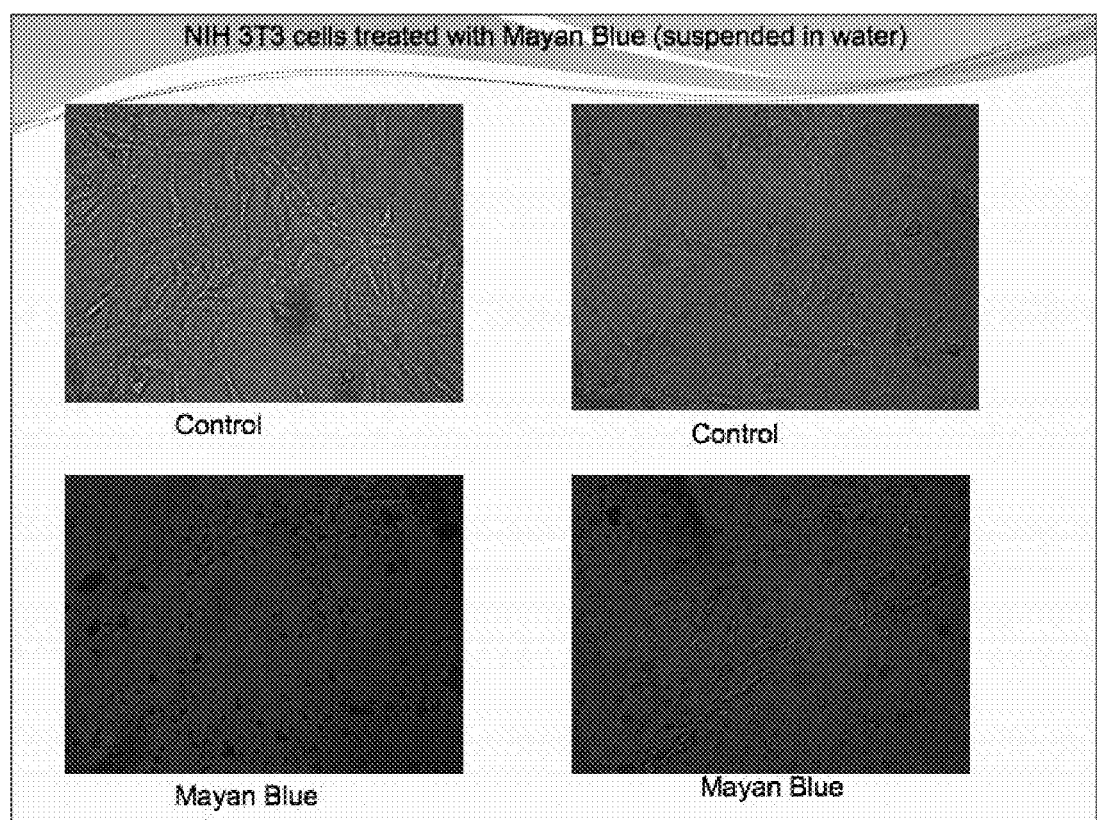
FIG. 11 shows NIH-3T3 cells treated with different concentrations of Organic/Inorganic Complex Materials Mayan Blue (suspended in water).
Figure 12:
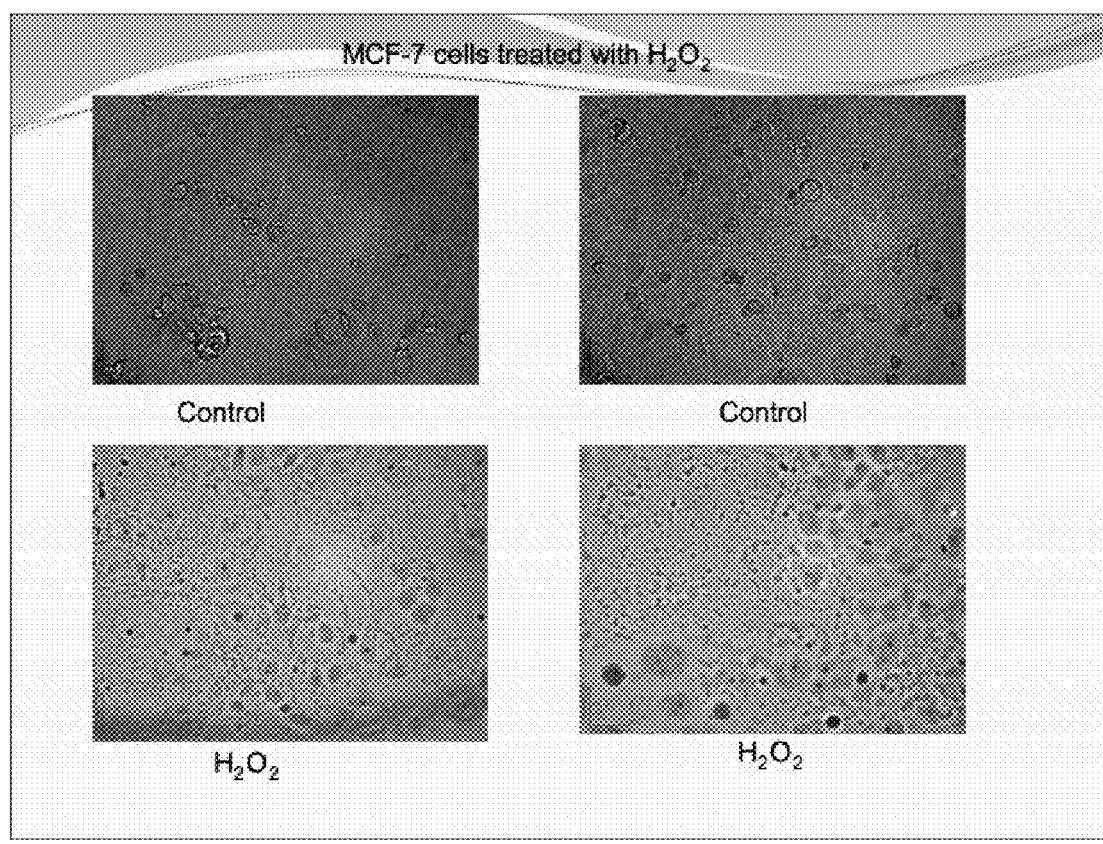
FIG. 12 shows MCF-7 cells treated with $H_2O_2$.
Figure 13:
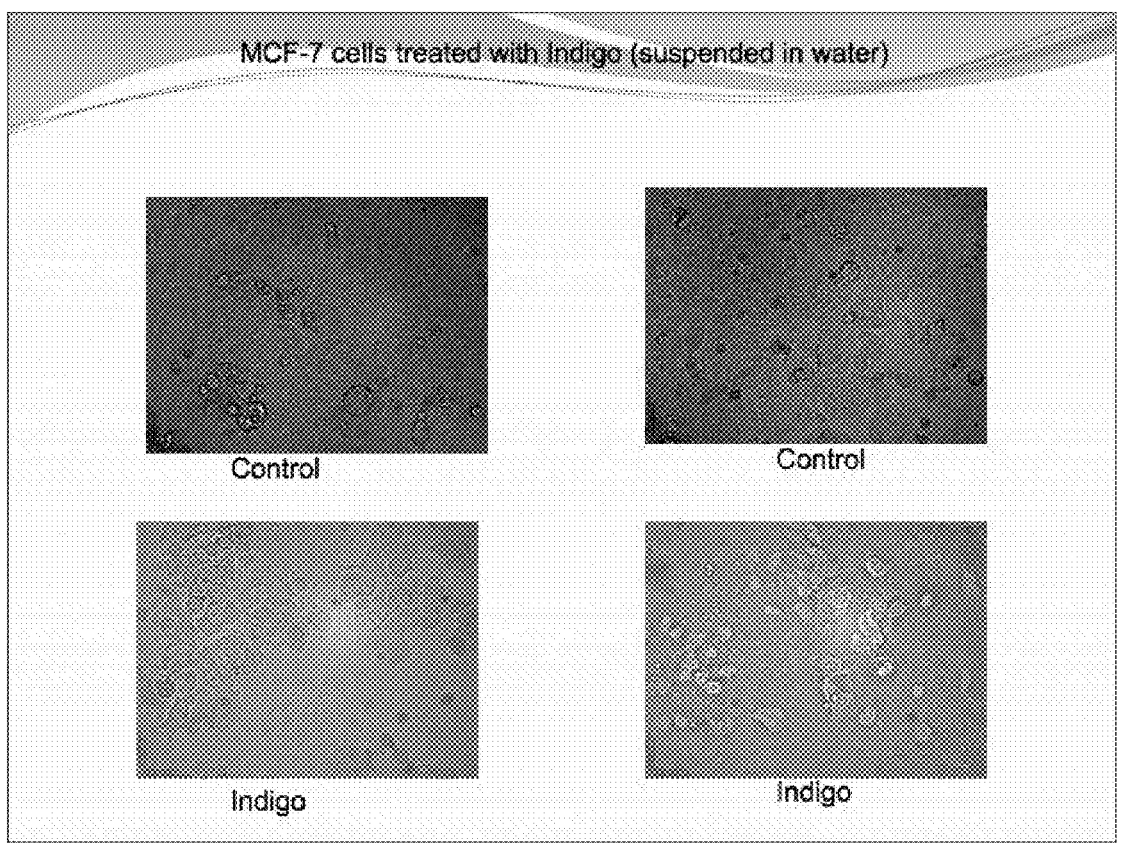
FIG. 13 shows MCF-7 cells treated with Indigo (suspended in water).
Figure 14:
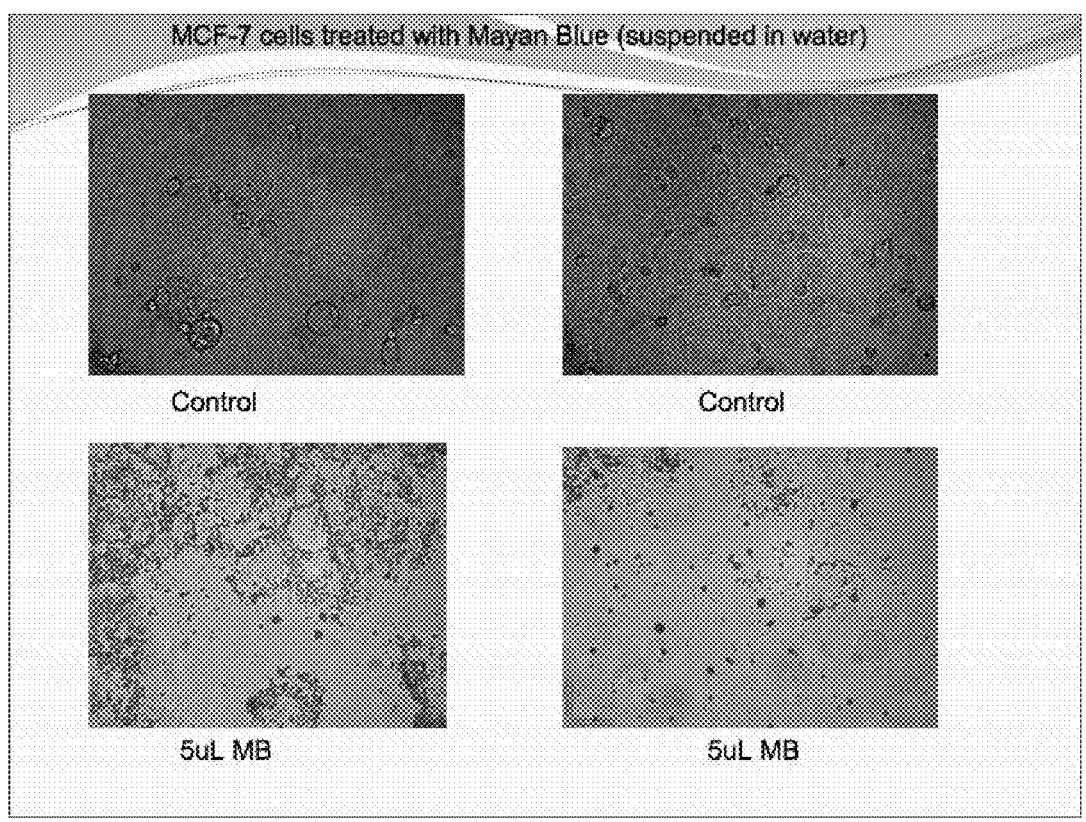
FIG. 14 shows MCF-7 cells treated with 5 uL of an Organic/Inorganic Complex Materials with Maya Blue (suspended in water).
Figure 15:
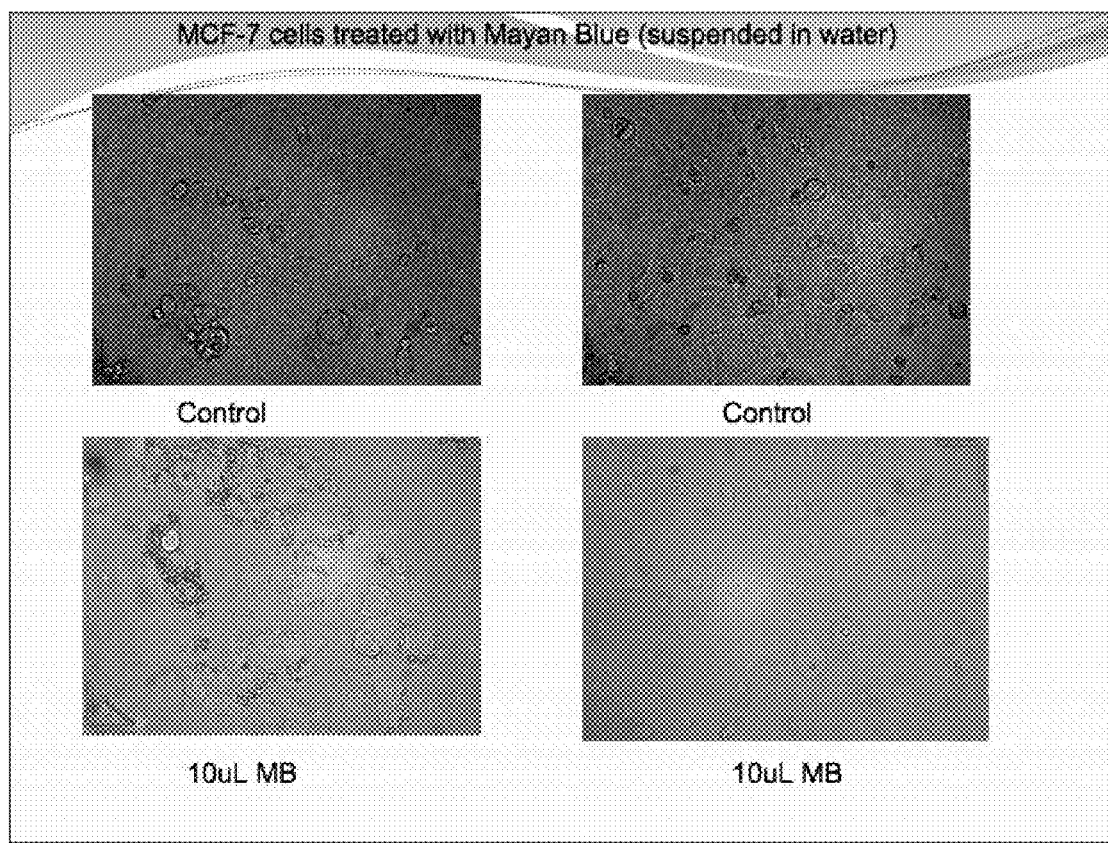
FIG. 15 shows MCF-7 cells treated with 10 uL of an Organic/Inorganic Complex Materials with Maya Blue (suspended in water).
Figure 16:
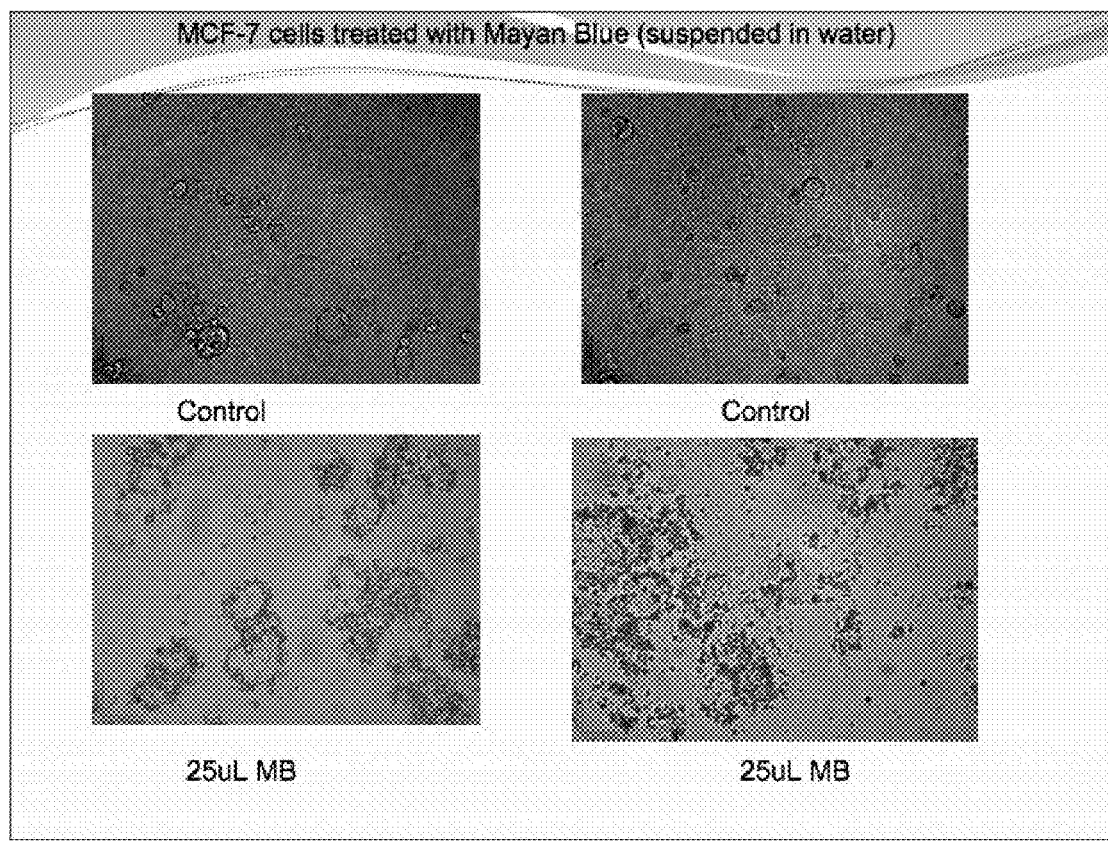
FIG. 16 shows MCF-7 cells treated with 25 uL of an Organic/Inorganic Complex Materials with Maya Blue (suspended in water).
Figure 17:
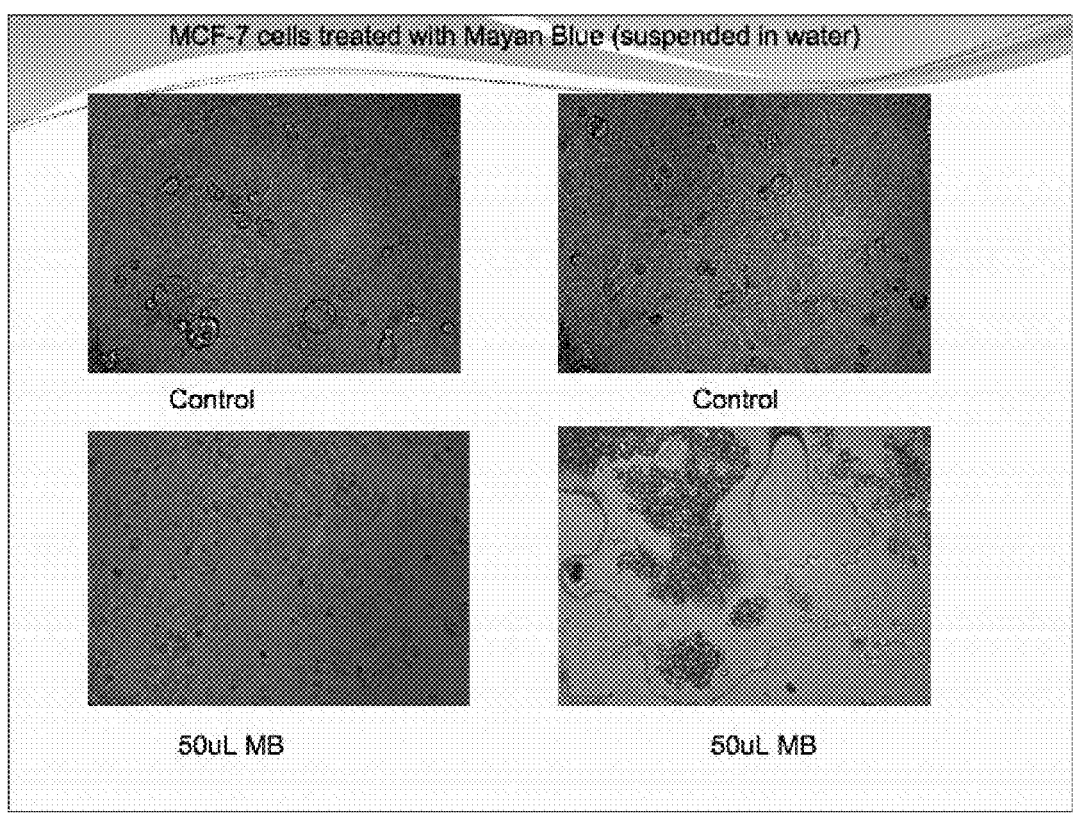
FIG. 17 shows MCF-7 cells treated with 50 uL of an Organic/Inorganic Complex Materials with Maya Blue (suspended in water).
Figure 18:
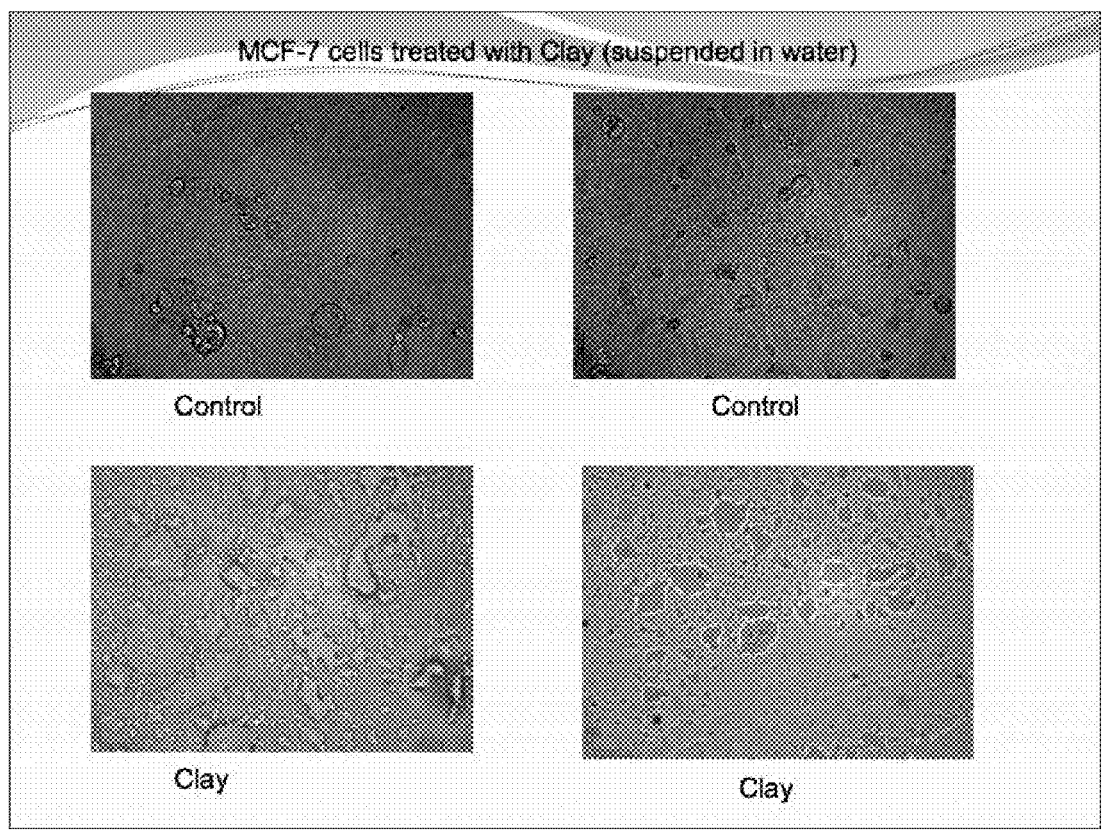
FIG. 18 shows MCF-7 cells treated with clay.
Figure 19:
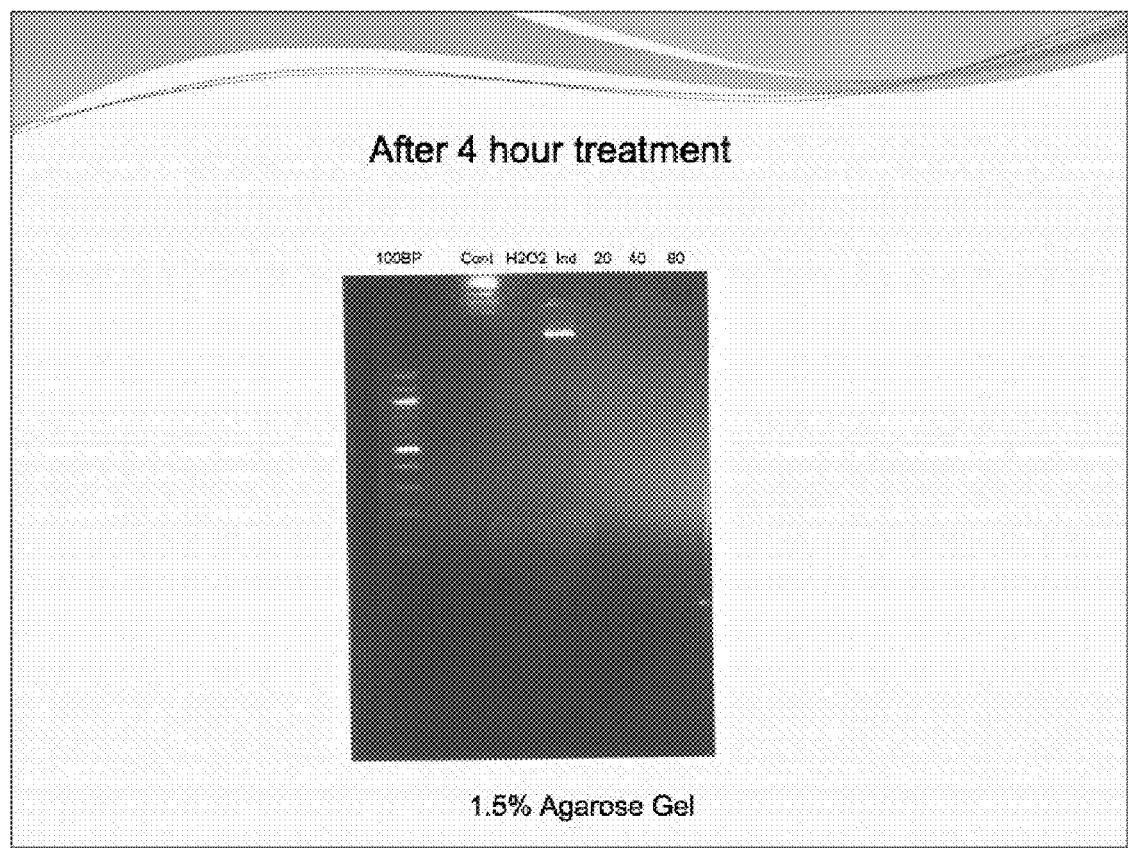
FIG. 19 is a 1.5% agarose gel of cells treated with controls and Mayan Blue (suspended in water) after 4 hours.
Figure 20:
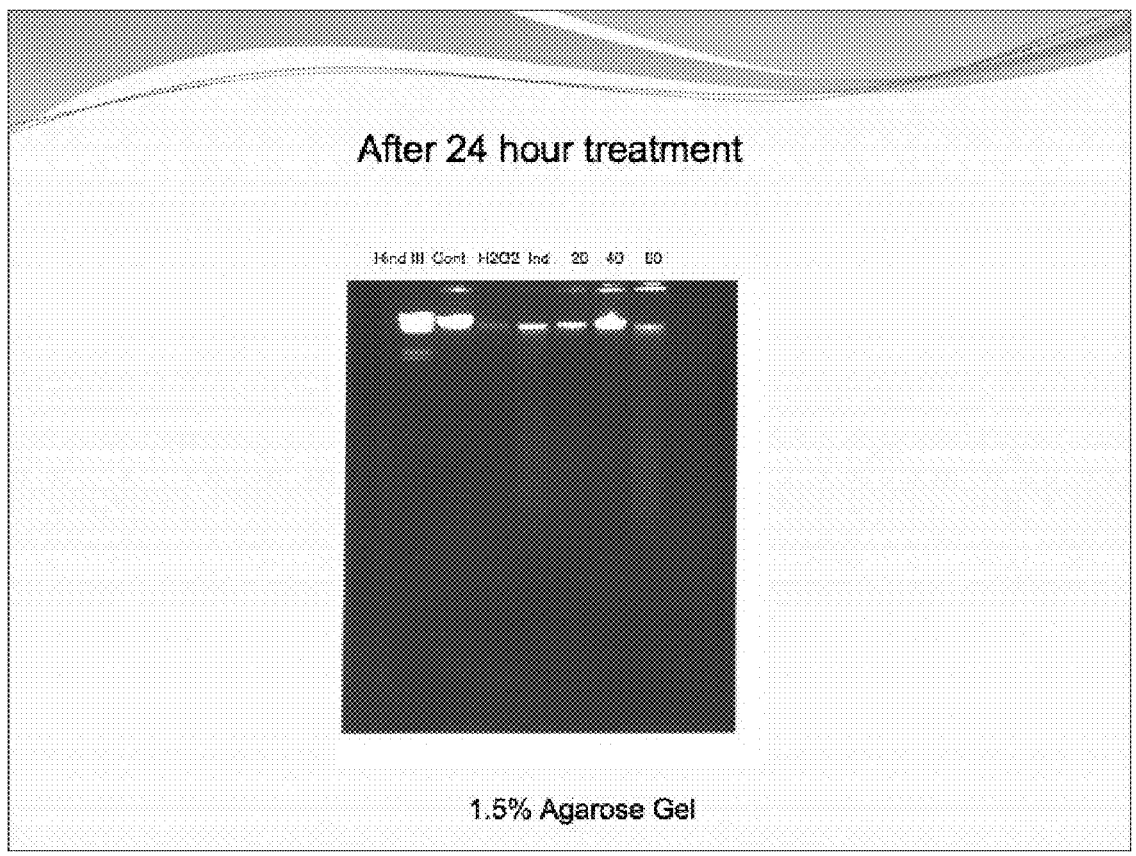
FIG. 20 is a 1.5% agarose gel of cells treated with controls and an Organic/Inorganic Complex Materials with Maya Blue (suspended in water) after 24 hours.

FIG. 9 shows NIH-3T3 cells treated with $H_2O_2$. FIG. 10 shows NIH-3T3 cells treated with Indigo (suspended in water). FIG. 11 shows NIH-3T3 cells treated with different concentrations of Organic/Inorganic Complex Materials with Maya Blue (suspended in water). FIG. 12 shows MCF-7 cells treated with $H_2O_2$. FIG. 13 shows MCF-7 cells treated with Indigo (suspended in water). FIG. 14 shows MCF-7 cells treated with 5 uL of Mayan Blue (suspended in water). FIG. 15 shows MCF-7 cells treated with 10 uL of Mayan Blue (suspended in water). FIG. 16 shows MCF-7 cells treated with 25 uL of Mayan Blue (suspended in water). FIG. 17 shows MCF-7 cells treated with 50 uL of Mayan Blue (suspended in water). FIG. 18 shows MCF-7 cells treated with clay. FIG. 19 is a 1.5% agarose gel of cells treated with controls and Mayan Blue (suspended in water) after 4 hours. FIG. 20 is a 1.5% agarose gel of cells treated with controls and Mayan Blue (suspended in water) after 24 hours.

Figure 21:
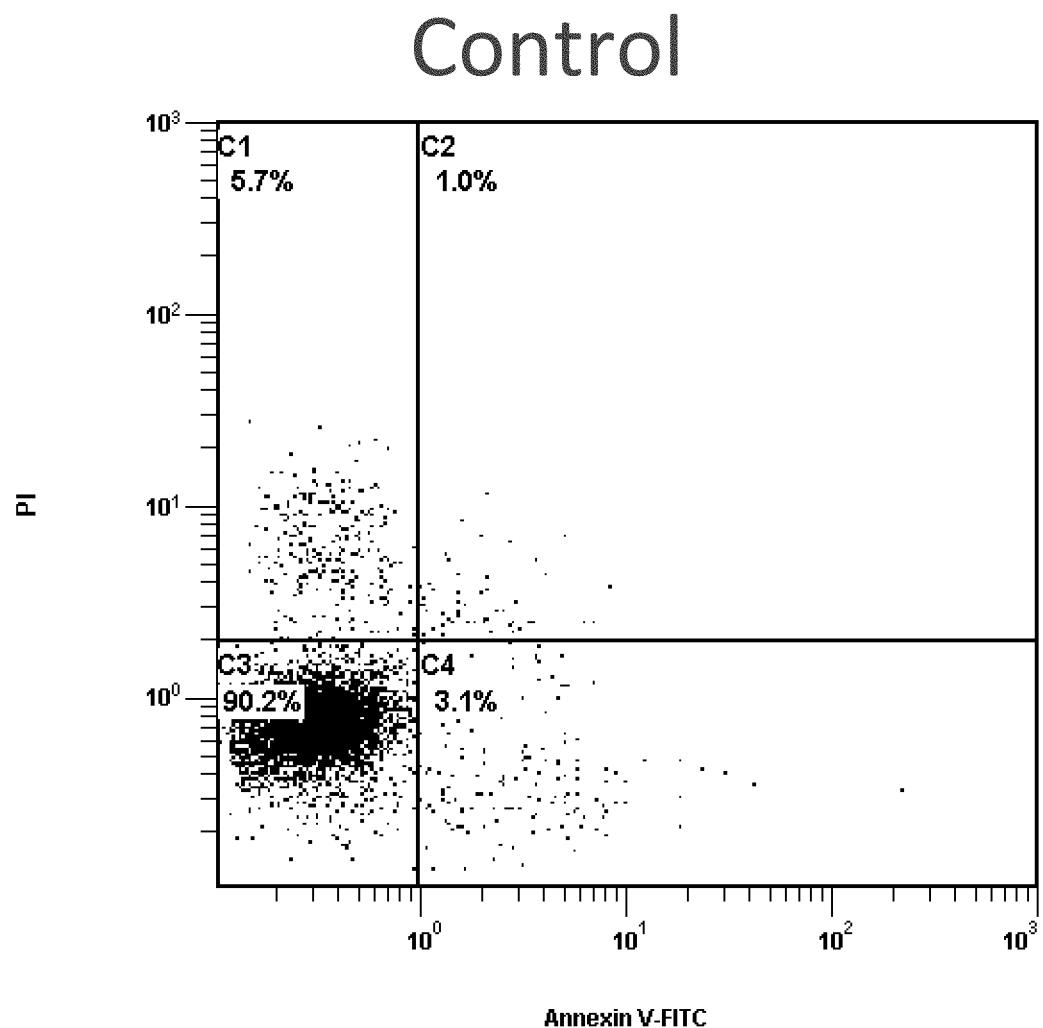
FIG. 21 is a Fluorescence Activated Cell Sorter (FACS) graph of Propidium iodide and Annexin V of control cells.
Figure 22:
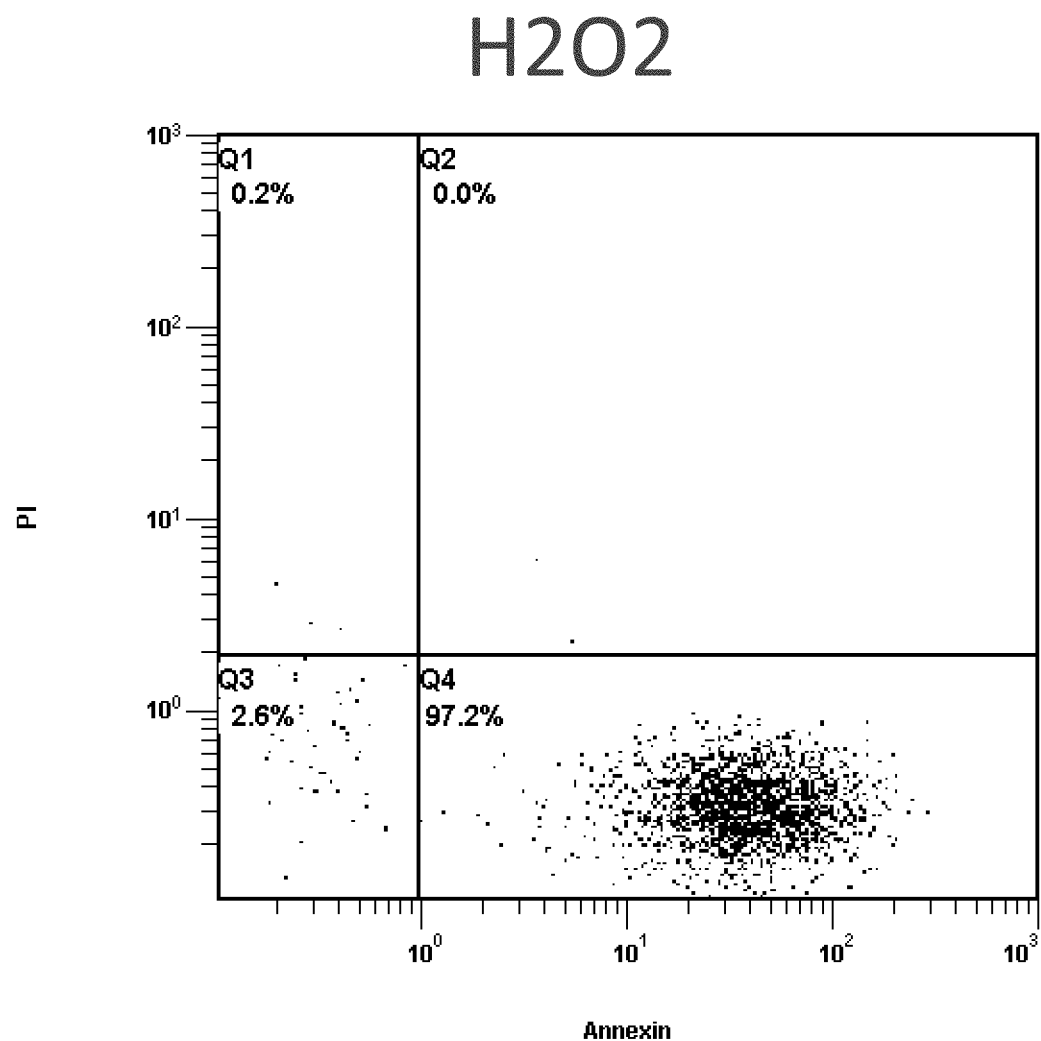
FIG. 22 is a Fluorescence Activated Cell Sorter (FACS) graph of Propidium iodide and Annexin V of cells treated with $H_2O_2$.
Figure 23:
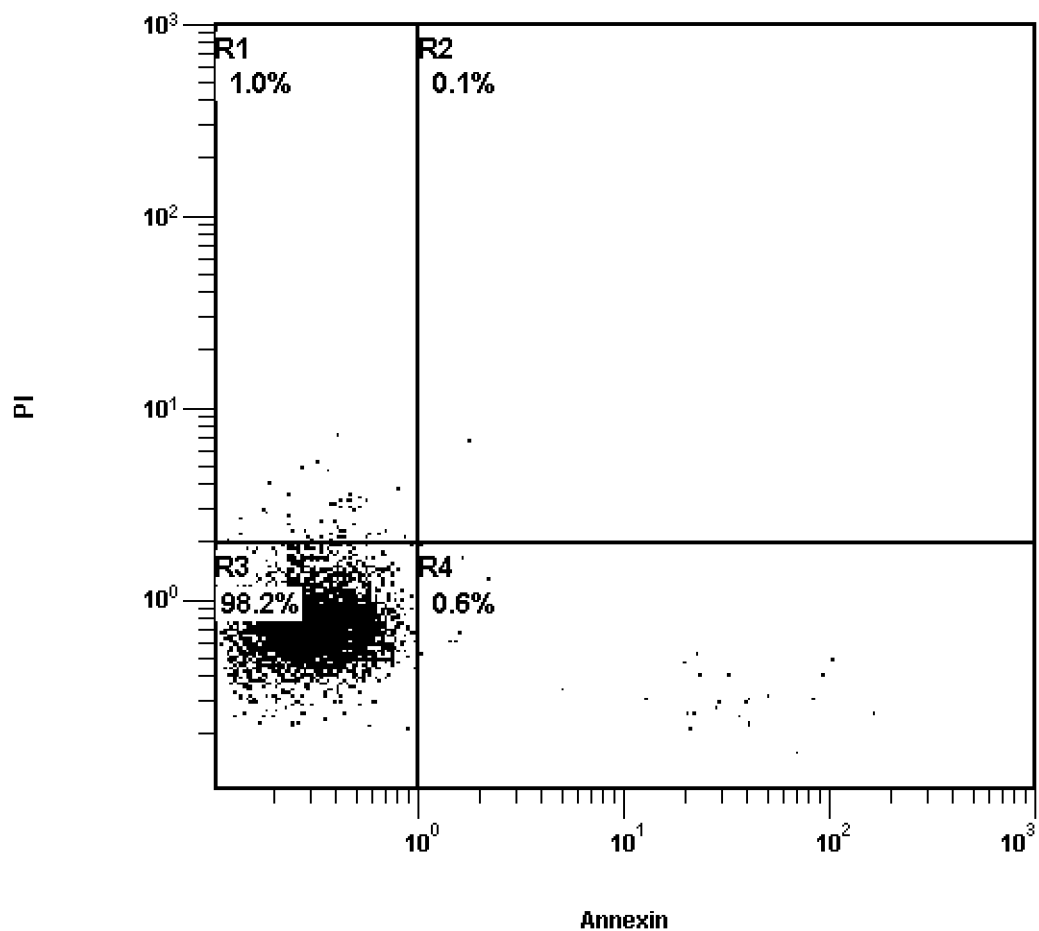
FIG. 23 is a Fluorescence Activated Cell Sorter (FACS) graph of Propidium iodide and Annexin V of cells treated with Clay alone.
Figure 24:
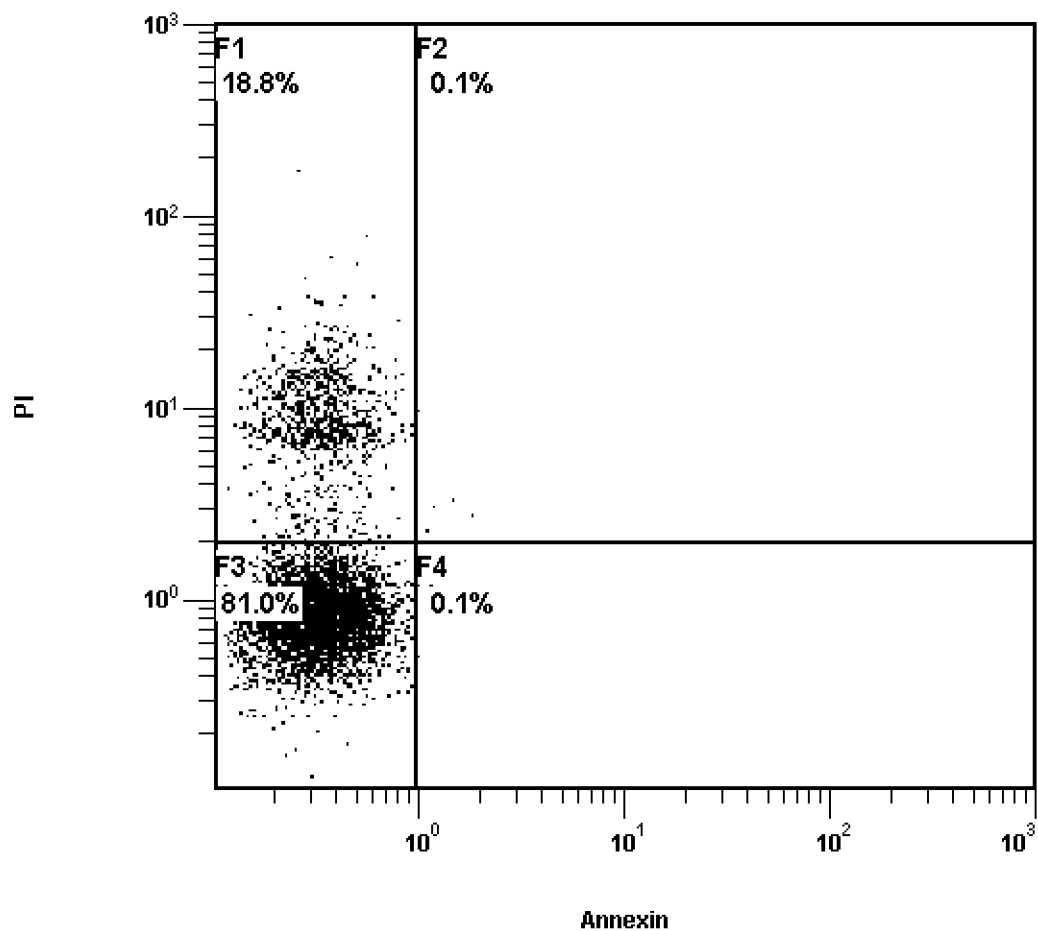
FIG. 24 is a Fluorescence Activated Cell Sorter (FACS) graph of Propidium iodide and Annexin V of cells treated with Indigo.
Figure 25:
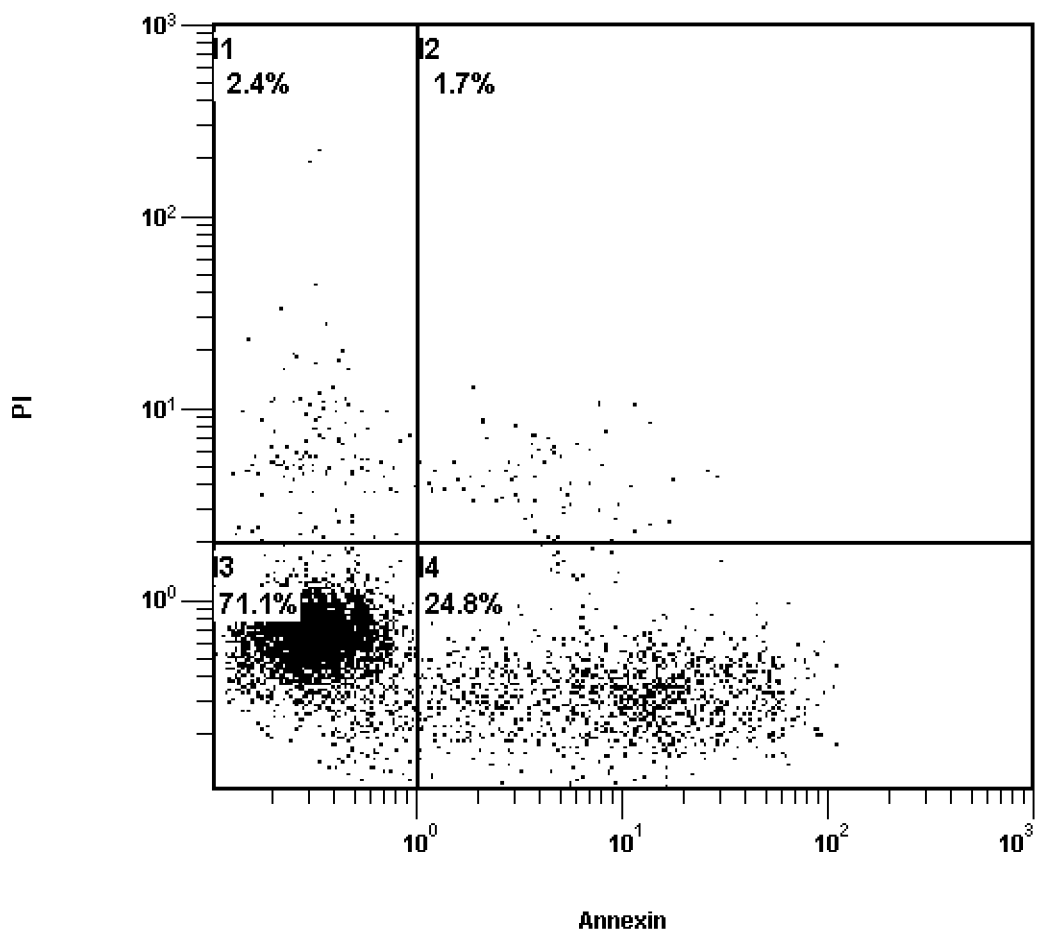
FIG. 25 is a Fluorescence Activated Cell Sorter (FACS) graph of Propidium iodide and Annexin V of cells treated with an Organic/Inorganic Complex Materials with Maya Blue at 2.5 uL.
Figure 26:
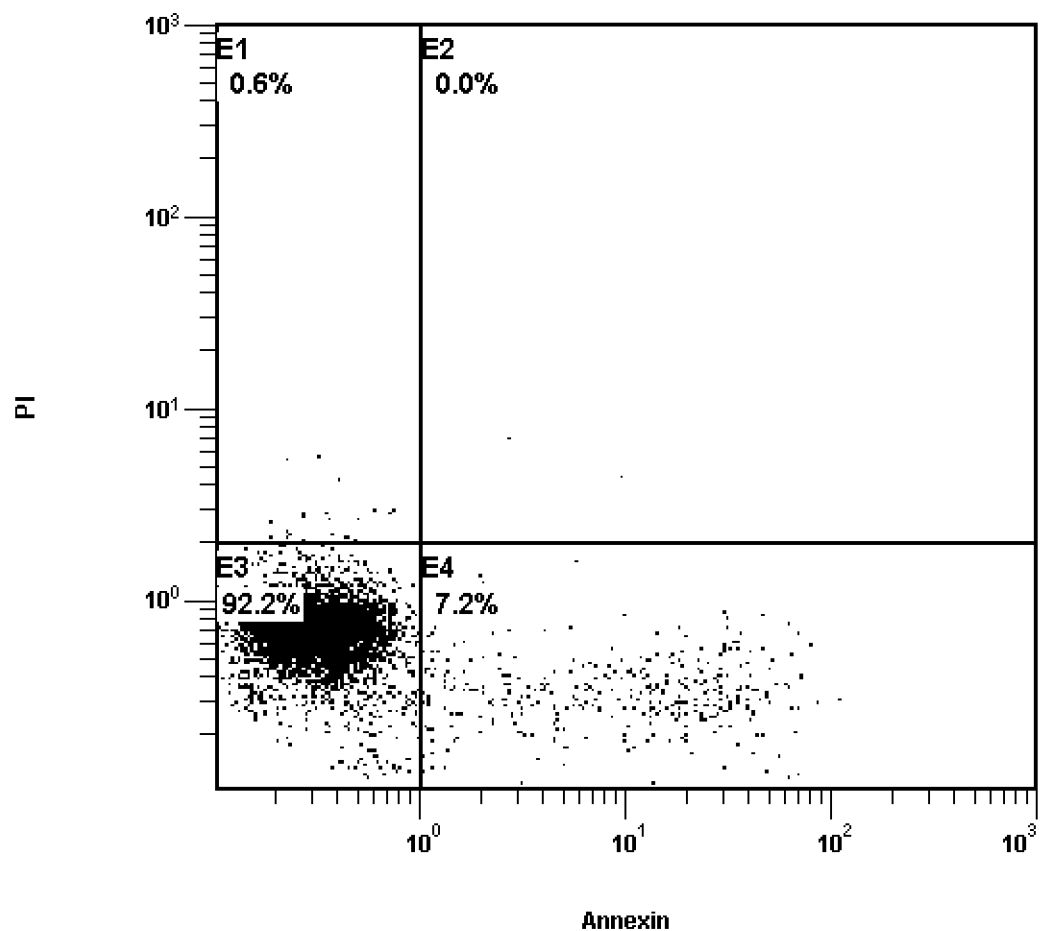
FIG. 26 is a Fluorescence Activated Cell Sorter (FACS) graph of Propidium iodide and Annexin V of cells treated with an Organic/Inorganic Complex Materials with Maya Blue at 12.5 uL.
Figure 27:
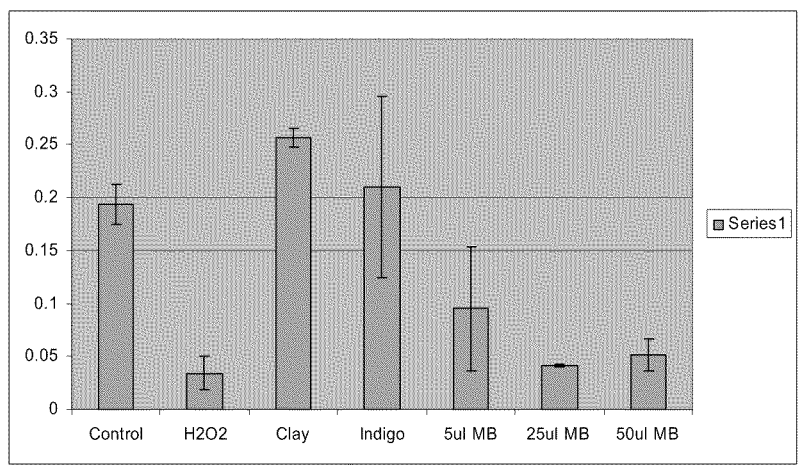
FIG. 27 is a graph that shows the relative effect of various conditions on cell viability.

FIG. 21 is a Fluorescence Activated Cell Sorter (FACS) graph of Propidium iodide and Annexin V of control cells. FIG. 22 is a Fluorescence Activated Cell Sorter (FACS) graph of Propidium iodide and Annexin V of cells treated with $H_2O_2$. FIG. 23 is a Fluorescence Activated Cell Sorter (FACS) graph of Propidium iodide and Annexin V of cells treated with Clay alone. FIG. 24 is a Fluorescence Activated Cell Sorter (FACS) graph of Propidium iodide and Annexin V of cells treated with Indigo. FIG. 25 is a Fluorescence Activated Cell Sorter (FACS) graph of Propidium iodide and Annexin V of cells treated with Mayan Blue at 2.5 uL. FIG. 26 is a Fluorescence Activated Cell Sorter (FACS) graph of Propidium iodide and Annexin V of cells treated with Mayan Blue at 12.5 uL. FIG. 27 is a graph that shows the relative effect of various conditions on cell viability.

Cell Culture—The human colon cancer cell line HT-29 were obtained from the American Type Culture Collection. They were cultured in T-25 flasks with McCoy's 5A Medium supplemented with 10% FBS and 10% PenStrep. The cells were then harvested from the flask and 100,000 cells were seeded in each well of a 12 well plate with 1 mL of media.

Cell Treatment—The purpose of treating the cells was to determine whether the Mayan Blue pigments had any effect in changing the morphology of the cells. Indigo and clay were also tested because the Organic/Inorganic Complex Materials with Maya Blue is composed of both clay and indigo. After the cells acquired an elongated morphology, they were treated with 3% Hydrogen Peroxide (positive control), 20 uL Dimethyl sulfoxide (second positive control), 20 uL clay (10 mg/mL DMSO), 5 uM, 10 uM, 25 uM, and 50 uM of indigo (7.6 mM), and 2 uL, 5 uL, 15 uL, 25 uL of Organic/Inorganic Complex Materials with Maya Blue (slurry was made 10 mg/mL of DMSO).

Cell Morphology Study—The purpose of looking at the cell morphology was to determine if there were any signs of apoptosis within the treated cells, as opposed to the control. After treating the cells for different time points (4 hours, 12 hours, 24 hours) they were observed under a light microscope and pictures were taken.

Fluorescence-activated cell sorting (FACS Assay)/Flow Cytometry Assay—The purpose of the Flow Cytometry Assay is not only to quantify the cells, but also to separate by analyzing the cell surface, characterizing cell types (apoptotic, necrotic, late apoptotic, and viable) in cell populations, and analyzing cell size.

The HT-29 cells were grown in two 12-well plates at a concentration of 100,000 cells/mL. They were incubated for 24 hours with different concentrations of Organic/Inorganic Complex Materials with Maya Blue or indigo. The supernatants from individual wells were then taken out and placed in FACS tubes ("flow tubes"). Then 300 uL of trypsin were added to each well and incubated for 5 minutes. Then detached cells with trypsin were collected and placed in the respective FACS tubes. The tubes were then centrifuged at 1400 rpm for 5 minutes at 4° C. to obtain a pellet. The media/trypsin solution was then discarded. The pellet was washed twice with 1×PBS, centrifugation process was repeated and the supernatant was discarded. Then 100 uL of Annexin V Binding Buffer was added to each pellet along with 5 uL of Annexin-V FITC and 5 uL of propidium iodide. (The purpose of Annexin-V FITC is to detect the cells that die apoptotically, and the purpose of propidium iodide is to detect the cells that die necrotically). Due to the photosensitivity of the Annexin-V FITC and the propidium iodide, this process must be performed in the dark.

Purification of Total DNA from cultured animal cells. The HT-29 cells were grown in two 6-well plates at a concentration of 1,000,000 cells/mL, they were treated with 3% Hydrogen Peroxide (positive control), 20 uL dimethyl sulfoxide (second positive control), 20 uL clay (10 mg/mL DMSO), and 2 uL, 5 uL, 15 uL, 20 uL, 40 uL and 60 uL of Mayan Blue pigments (slurry was made 10 mg/mL of DMSO) for 24 hours. Treated HT-29 cells were centrifuged in DNeasy Mini Spin Columns for 5 minutes at 300×g. The maximum number of cells was no greater than $5 \times 10^6$. Freezing the cells overnight is optional. The thawed cells were resuspended in 200 uL of Phosphate Buffered Saline (0.8 g NaCl, 0.2 g KCl, 1.44 g $Na_2HPO_4$, 0.24 g $KH_2PO_4$ in 800 ml of distilled $H_2O$). Then 20 uL of Proteinase K and 200 uL of Buffer AL were added to the sample, making sure not to add Proteinase K directly to Buffer AL. The solution was vortexed immediately and incubated at 70° C. for 10 minutes. Following this, 200 uL of ethanol (96-100%) were added to the sample and vortexed to yield a homogenous solution. If a white precipitate formed, it was added with solution. The homogenous solution was pipetted into DNeasy Mini Spin column and placed in a new 2 mL collection tube. Buffer AW1 was added (500 uL), then centrifuged for 1 minute at 8000 rpm. Flow through and collection tubes were discarded. Then 500 uL of Buffer AW2 were added and centrifuged for 3 minutes at 14000 rpm to dry DNeasy membrane. Flow through and collection tubes were discarded. DNeasy Mini Spin column were placed in a clean 1.5 mL/2 mL microcentrifuge tube. Buffer AE (200 uL) were pipetted directly into the DNeasy membrane and incubated at room temperature for 1 minute. The tubes were then centrifuged for 1 minute at 8000 rpm to elute.

Table 1 shows the effect of Organic/Inorganic Complex Pigment with Mayan Blue on tumors. The listed tumors were injected into animals and the animals were treated with treated with the concentrations of the various pigments listed. The percent inhibition demonstrates the effect of the OICM of the present invention is listed.

Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and

TABLE 1

Effect of Organic/Inorganic Complex Pigment with Mayan Blue on Tumors.

| Tumor | Group | Dose (mg/kg × d) | No. of animals | Tumor Size X ± SD | Inhibition (%) | Statistic Test (ST test) |
|---|---|---|---|---|---|---|
| LLC | control | — | 10 | 3.5 ± 0.44 | 0 | |
| LLC | Indirubin | 100 × 9 | 10 | 2.58 ± 0.21 | 26.3 ± 2.8 | P < 0.05 |
| LLC | Meisoindigo | 106 × 9 | 10 | 1.80 ± 0.15 | 48.6 ± 4.1 | P < 0.01 |
| Walker 256 | control | — | 10 | 9.7 ± 1.02 | 0 | |
| Walker 256 | Indirubin | 100 × 9 | 10 | 3.94 ± 0.71 | 59.4 ± 2.9 | P < 0.01 |
| Walker 256 | Meisoindigo | 106 × 9 | 10 | 2.10 ± 0.17 | 71.6 ± 3.1 | P < 0.01 |

It is contemplated that any embodiment discussed in this specification can be implemented with respect to any method, kit, reagent, or composition of the invention, and vice versa.

so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES www.mexicanmercados.com/produce/mediherb.html
www.hort.purdue.edu/newcrop/med-aro/factsheets/INDIGO.html

What is claimed is:

1. A method of treating cancer comprising contacting the cancer with a composition comprising a therapeutically effective amount of a treated organic/inorganic complex material comprising an indigo dye and an inorganic fibrous clay material, in a pharmaceutically acceptable carrier, in which the indigo dye and the inorganic fibrous clay material are connected by a stabilized organic and inorganic bond formed by heating the indigo dye and the inorganic fibrous clay material or exposing them to UV light such that the molecular properties of the indigo dye and the inorganic fibrous clay material are changed to enhance a cancer suppression ability of the composition, and wherein the cancer is selected from the group consisting of stomach cancer, colon cancer and breast cancer.

2. The method of claim 1, wherein the effective amount is 10 to 3,000 mg/kg.

3. The method of claim 1, wherein the composition is micronized and is suitable for administration to the warm blooded animal by injection.

4. The method of claim 1, wherein the composition is administered in an amount of from 10 mg/kg body weight to 10,000 mg/kg body weight.

5. The method of claim 1, wherein the composition is administered orally, enterically, intravenously, peritoneally, parenterally or subcutaneously.

6. The method of claim 1, wherein the cancer involves metastasis.

7. The method of claim 1, wherein the composition further comprise a safe and effective amount of a second chemotherapeutic agent.

8. A method for treating an animal having a cancer of the stomach, colon or breast, comprising administering to the animal a therapeutically effective amount of a treated organic/inorganic complex material that comprises an indigo dye and an inorganic fibrous clay material, in a pharmaceutically acceptable carrier to induce necrosis in at least a portion of the cancer, to induce cancer regression or to induce cancer remission, in which the indigo dye and the inorganic fibrous clay material are connected by a stabilized organic and inorganic bond formed by heating the indigo dye and the inorganic fibrous clay material or exposing them to UV light such that the molecular properties of the indigo dye and the inorganic fibrous clay material are changed to enhance a cancer suppression ability of the composition.

9. The method of claim 8, wherein the effective amount is 10 to 3,000 mg/kg.

10. The method of claim 8, wherein the composition is micronized and is suitable for administration to the warm blooded animal by injection.

11. The method of claim 8, wherein the composition is administered in an amount of from 10 mg/kg body weight to 10,000 mg/kg body weight.

12. The method of claim 8, wherein the composition is administered orally, enterically, intravenously, peritoneally, parenterally or subcutaneously.

13. The method of claim 8, wherein the cancer involves metastasis.

14. The method of claim 8, further comprising a safe and effective amount of a second chemotherapeutic agent.

15. A method of treating a cancer comprising administering to a subject in need thereof an effective amount of a composition comprising a therapeutically effective amount of a treated organic/inorganic complex that comprises an indigo dye and an inorganic fibrous clay material, in a pharmaceutically acceptable carrier, in which the indigo dye and the inorganic fibrous clay material are connected by a stabilized organic and inorganic bond formed by heating the indigo dye and the inorganic fibrous clay material or exposing them to UV light such that the molecular properties of the indigo dye and the inorganic fibrous clay material are changed to enhance a cancer suppression ability of the composition, wherein said cancer is selected from the group consisting of a stomach, colon or breast cancer.

16. A method for treating disorders of the skin or mucosa resulting from cancer therapies comprising:
identifying a patient receiving cancer treatment; and
administering to the patient an effective dose of an organic/inorganic complex that comprises an indigo dye and an inorganic fibrous clay material, in a pharmaceutically acceptable carrier, in which the indigo dye and the inorganic fibrous clay material are connected by a stabilized organic and inorganic bond formed by heating the indigo dye and the inorganic fibrous clay material or exposing them to UV light such that the molecular properties of the indigo dye and the inorganic fibrous clay material are changed to enhance a cancer suppression ability of the composition, wherein the cancer is selected from the group consisting of stomach cancer, colon cancer and breast cancer.

* * * * *